United States Patent
Shin et al.

(10) Patent No.: US 8,329,442 B2
(45) Date of Patent: Dec. 11, 2012

(54) SALMONELLA BACTERIOPHAGE AND ANTIBACTERIAL COMPOSITION COMPRISING THE SAME

(75) Inventors: Soo An Shin, Seoul (KR); Min Tae Park, Seoul (KR); Hyang Choi, Anyang-si (KR); Young Wook Cho, Seoul (KR); In Hye Kang, Suwon-si (KR); Su Jin Choi, Daegu (KR)

(73) Assignee: CJ Cheiljedang Corporation, Seoul (KR)

( * ) Notice: Subject to any disclaimer, the term of this patent is extended or adjusted under 35 U.S.C. 154(b) by 116 days.

(21) Appl. No.: 12/876,016

(22) Filed: Sep. 3, 2010

(65) Prior Publication Data

US 2011/0052544 A1     Mar. 3, 2011

Related U.S. Application Data

(60) Provisional application No. 61/239,748, filed on Sep. 3, 2009.

(51) Int. Cl.
*C12N 7/00* (2006.01)
(52) U.S. Cl. .................................................. 435/235.1
(58) Field of Classification Search .................. None
See application file for complete search history.

(56) References Cited

U.S. PATENT DOCUMENTS 6,485,902 B2  11/2002  Waddell et al.
6,942,858 B1   9/2005  Ghanbari et al.

OTHER PUBLICATIONS

Al-Tarazi et al., Asian-Aust. J. Anim. Sci., 2003, 16(1):77-82.*
Zoonoses Report, 2003, pp. 1-71, United Kingdom.

* cited by examiner

*Primary Examiner* — Zachariah Lucas
*Assistant Examiner* — Nicole Kinsey White
(74) *Attorney, Agent, or Firm* — Knobbe, Martens, Olson & Bear, LLP

(57) ABSTRACT

Disclosed herein are is a novel bacteriophage which has specific bactericidal activity against one or more *Salmonella* bacteria selected from the group consisting of *Salmonella Enteritidis, Salmonella Typhimurium, Salmonella Gallinarum*, and *Salmonella* Pullorum without affecting beneficial bacteria. Disclosed are also compositions, animal feeds or drinking water, cleaners and sanitizers for preventing and treating the infectious diseases caused by *Salmonella Enteritidis, Salmonella Typhimurium, Salmonella Gallinarum* or *Salmonella* Pullorum including salmonellosis, *Salmonella* food poisoning, Fowl Typhoid, and Pullorum disease or for controlling the *salmonella* bacteria.

8 Claims, 9 Drawing Sheets

Figure 5
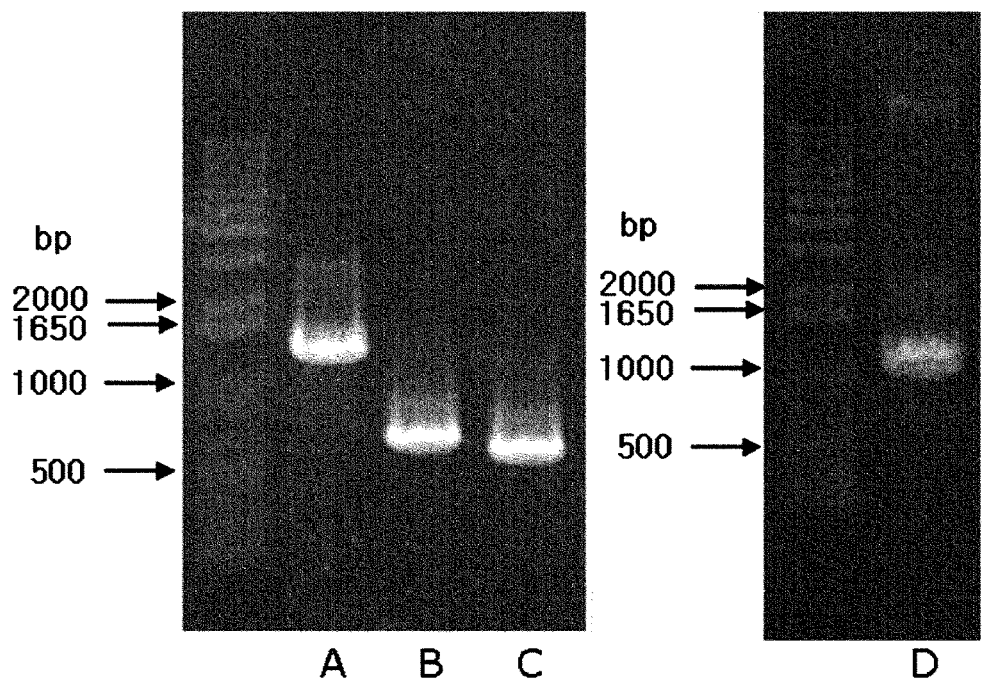
【Figure 6】
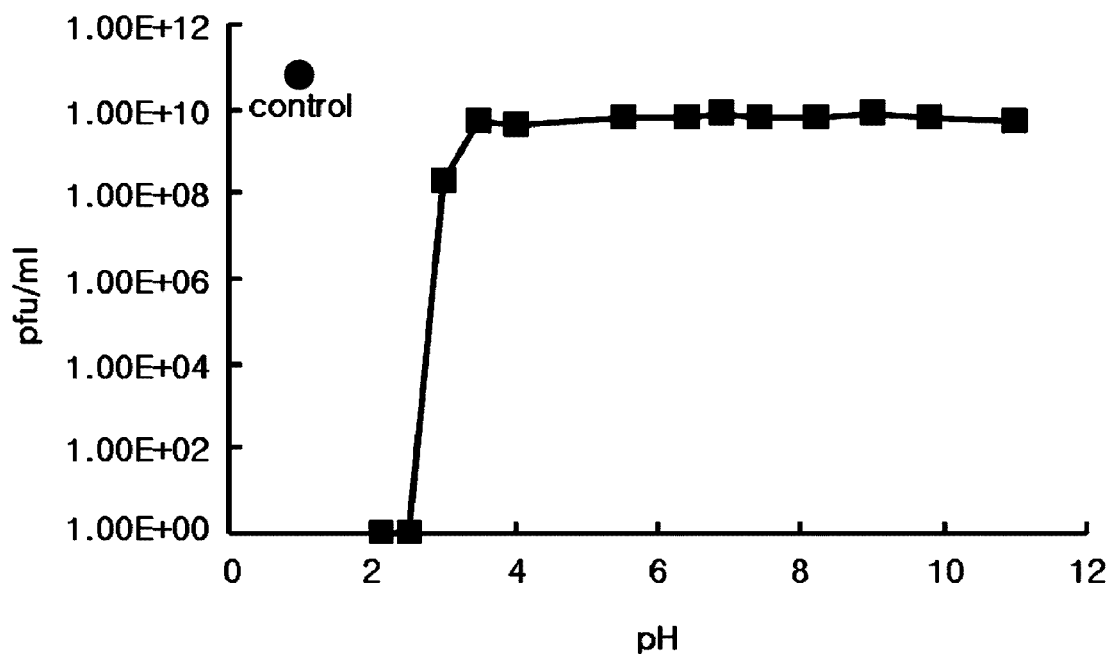

SALMONELLA BACTERIOPHAGE AND ANTIBACTERIAL COMPOSITION COMPRISING THE SAME

CROSS-REFERENCE TO RELATED PATENT APPLICATION

This application claims the benefit of U.S. Provisional Application No. 61/239,748 filed on Sep. 3, 2009, the disclosure of which is hereby expressly incorporated by reference in its entirety and hereby expressly made a portion of this application.

TECHNICAL FIELD

The present invention relates to a novel bacteriophage and antibacterial composition comprising the same.

BACKGROUND ART

*Salmonella* is a genus of the family Enterobacteriaceae, characterized as Gram-negative, facultatively anaerobic, non spore-forming, rod-shaped bacteria, and most strains are motile by flagella. *Salmonella* has an average genomic GC content of 50-52%, which is similar to that of *Escherichia coli* and *Shigella*. The genus *Salmonella* is a pathogenic microorganism that causes infections in livestock as well as in humans. Serological division has it that *Salmonella enterica*, a species of *Salmonella* bacterium, has a variety of serovars including Gallinarum, Pullorum, Typhimurium, Enteritidis, Typhi, Choleraesuis, and derby (Bopp C A, Brenner F W, Wells J G, Strokebine N A. *Escherichia, Shigella, Salmonella*. In Murry P R, Baron E J, et al., eds. *Manual of Clinical Microbiology*. 7th ed. Washington D.C. American Society for Microbiology 1999; 467-74; Ryan K J. Ray C G (editors) (2004). *Sherris Medical Microbiology* (4th ed). McGraw Hill. ISBN 0-8385-8529-9.). Of them, *Salmonella Gallinarum* and Pullorum are fowl-adapted pathogens, *Salmonella Typhi* is a human-adapted pathogen, *Salmonella* Choleraesuis and *Salmonella* derby are swine-adapted pathogens, and *Salmonella* Enteritis and *Salmonella Typhimurium* are pathogenic for humans and animals. Each serovar causes illness in the respective species, resulting in tremendous damage to farmers or consumers.

A disease of domestic birds caused by *Salmonella bacterium* is Fowl Typhoid (FT), which is caused by a pathogen, *Salmonella Gallinarum* (hereinafter, referred to as "SG"). Fowl Typhoid (FT) is a septicemic disease of domestic birds such as chicken and turkey, and the course may be acute or chronic with high mortality. A recent report has had it that Fowl Typhoid frequently occurs in Europe, South America, Africa, and Southeast Asia, with damages increasing every year. Outbreaks of FT in South Korea have been reported since 1992 and economic losses caused by FT in brown, egg-laying chickens are very serious (Kwon Yong-Kook. 2000 annual report on avian diseases. Information publication by National Veterinary Research & Quarantine Service. March, 2001; Kim Ae-Ran et al., The prevalence of pullorum disease-fowl typhoid in grandparent stock and parent stock in Korea, 2003, Korean J Vet Res (2006) 46(4): 347-353).

Pullorum disease is also caused by a strain of the *Salmonella* bacteria, *Salmonella* Pullorum (hereinafter, referred to as "SP"). Pullorum disease occurs in any age or season, but young chickens are particularly susceptible to the disease. During the past century, it has been a serious disease among young chickens at 1-2 weeks of age or younger. Since the 1980s, the occurrence has greatly decreased. However, it has been growing since the mid-1990s (Kwon Yong-Kook. 2000 annual report on avian diseases. Information publication by National Veterinary Research & Quarantine Service. March, 2001; Kim Ae-Ran et al., The prevalence of pullorum disease-fowl typhoid in grandparent stock and parent stock in Korea, 2003, Korean J Vet Res (2006) 46(4): 347~353).

In South Korea, outbreaks of Fowl Typhoid and Pullorum disease have been increasing since the 1990s, inflicting economic damages on farmers. For this reason, a live attenuated SG vaccine has been used in broilers for the prevention of Fowl Typhoid from 2004 (Kim Ae-Ran et al., The prevalence of pullorum disease-fowl typhoid in grandparent stock and parent stock in Korea, 2003, Korean J Vet Res (2006) 46(4): 347-353). Its efficacy is doubtful, and the live vaccine is not allowed to be used for layers because of the risk of egg-transmitted infections. Unfortunately, there are still no commercially available preventive strategies against Pullorum disease, unlike Fowl Typhoid. Thus, there is an urgent need for new ways to prevent Fowl Typhoid and Pullorum disease.

Meanwhile, *Salmonella Enteritidis* (hereinafter, referred to as "SE") and *Salmonella Typhimurium* (hereinafter, referred to as "ST") are zoonotic pathogens, which show no host specificity, unlike SG or SP (Zoobises Report; United Kingdom 2003).

SE and ST are causative of salmonellosis in poultry, pigs, and cattle. Salmonellosis, caused by Salmonella bacteria, is an acute or chronic infection of the digestive tract in livestock, and shows the major symptoms of fever, enteritis, and septicemia, occasionally pneumonia, arthritis, abortion, and mastitis. Salmonellosis occurs worldwide, and most frequently during the summer months (T. R. Callaway et al. Gastrointestinal microbial ecology and the safety of the food supply as related to Salmonella. J Anim Sci 2008.86:E163-E172). In cattle, typical symptoms include loss of appetite, fever, dark brown diarrhea or bloody mucous in stool. The acute infection in calves leads to rapid death, and the infection during pregnancy leads to fetal death due to septicemia, resulting in premature abortion. In pigs, salmonellosis is characterized clinically by three major syndromes: acute septicemia, acute enteritis, and chronic enteritis. Acute septicemia occurs in 2~4-month-old piglets, and death usually occurs within 2~4 days after onset of symptoms. Acute enteritis occurs during the fattening period, and is accompanied by diarrhea, high fever, pneumonia, and nervous signs. Discoloration of the skin may occur in some severe cases. Chronic enteritis is accompanied by continuing diarrhea.

Once an outbreak of salmonellosis by SE and ST occurs in poultry, pigs, and cattle, it is difficult to cure only with therapeutic agents. The reasons are that *Salmonella* bacteria exhibit a strong resistance to various drugs and live in cells that are impermeable to antibiotics upon the occurrence of clinical symptoms. Up to now, there have been no methods for effectively treating salmonellosis caused by SE and ST, including antibiotics.

As in livestock, SE and ST cause infections in humans via livestock and their products, leading to *salmonella* food poisoning. Intake of infected, improperly cooked livestock products (e.g., meat products, poultry products, eggs and by-products) infects humans. *Salmonella* food poisoning in humans usually involves the prompt onset of headache, fever, abdominal pain, diarrhea, nausea, and vomiting. The symptoms commonly appear within 6-72 hours after the ingestion of the organism, and may persist for as long as 4-7 days or even longer (NSW+HEALTH. 2008, January 14.).

According to a report by the CDC (The Centers for Disease Control and Prevention, USA), 16% of human food poisoning outbreaks between 2005 and 2008 were attributed to Salmonella bacteria, with SE and ST responsible for 20% and 18% thereof, respectively. With respect to salmonella food poisoning in humans between 1973 and 1984, the implicated food vehicles of transmission were reportedly chicken (5%), beef (19%), pork (7%), dairy products (6%), and turkey (9%). In 1974~1984, the bacterial contamination test on broilers during the slaughter process showed 35% or more of salmonella incidence. In 1983, salmonella was isolated in 50.6% of chicken, 68.8% of turkey, 60% of goose, 11.6% of pork, and 1.5% of beef. Further, a survey carried out in 2007 reported that salmonella was found in 5.5% of raw poultry meat and 1.1% of raw pork. In particular, it was revealed that SE commonly originated from contaminated egg or poultry meat, and ST from contaminated pork, poultry meat, and beef (Centers for Disease Control and Prevention (CDC)). For example, food poisoning caused by SE has rapidly increased in the US, Canada, and Europe since 1988, and epidemiological studies demonstrated that it was attributed to eggs or egg-containing foods (Agre-Food Safety Information Service(AGROS). Domestic and foreign food poisoning occurrence and management trend. 2008. 02). A risk assessment conducted by FAO and WHO in 2002 noted that the human incidence of salmonellosis transmitted through eggs and poultry meat appeared to have a linear relationship to the observed Salmonella prevalence in poultry. This means that, when reducing the prevalence of Salmonella in poultry, the incidence of salmonellosis in humans will fall (Salmonella control at the source; World Health Organization. International Food Safety Authorities Network (INFOSAN) Information Note No. 03/2007). Recently, fears about food safety have been spurred by outbreaks of salmonella from products as varied as peanuts, spinach, tomatoes, pistachios, peppers and, most recently, cookie dough (Jane Black and Ed O'Keefe. Overhaul of Food Safety Rules in the Works. Washington Post Staff Writers Wednesday, Jul. 8, 2009).

For these reasons, Salmonella infections must be reported in Germany (6 and 7 of the German law on infectious disease prevention, Infektionsschutzgesetz). Between 1990 and 2005 the number of officially recorded cases decreased from approximately 200,000 cases to approximately 50,000. It is estimated that every fifth person in Germany is a carrier of Salmonella. In the USA, there are approximately 40,000 cases of Salmonella infection reported each year.

Therefore, there is an urgent need to control SE and ST, which cause salmonellosis in livestock and humans. The collaborative efforts of USDA and FDA have developed a number of effective strategies to prevent salmonellosis that causes over 1 million cases of food-borne illness in the United States. Among them is a final rule, issued by the FDA, to reduce the contamination in eggs. The FDA will now require that egg producers test regularly for lethal *salmonella* during egg production, storage and shipment. As a result, an estimated 79,000 illnesses and 30 deaths due to contaminated eggs will be avoided each year (Jane Black and Ed O'Keefe. Overhaul of Food Safety Rules in the Works. *Washington Post* Staff Writers Wednesday, Jul. 8, 2009). In Denmark, conservative estimates from a cost benefit analysis comparing *Salmonella* control costs in the production sector with the overall public health costs of salmonellosis suggest that *Salmonella* control measures saved Danish society US$ 14.1 million in the year 2001 (Salmonella control at the source. World Health Organization. International Food Safety Authorities Network (INFOSAN) Information Note No. 03/2007).

Meanwhile, bacteriophage is a specialized type of virus that infects and destroys only bacteria, and can self-replicate only inside host bacteria. Bacteriophage consists of genetic material in the form of single or double stranded DNA or RNA surrounded by a protein shell. Bacteriophages are classified into three basic structural forms: an icosahedral (twenty-sided) head with a tail; an icosahedral head without a tail; and a filamentous form. Based on their tail structure, the most abundant form bacteriophages, which have an icosahedral head with a tail, are further divided into: Myoviridae, Siphoviridae, and Podoviridae, which are characterized by contractile, long non-contractile, and short noncontractile tails, respectively. Bacteriophages having an icosahedral head without a tail are divided based on their head shape and components, and the presence of shell. Filamentous bacteriophages having DNA as their genetic material are divided based on their size, shape, shell, and filament components (H. W. Ackermann. Frequency of morphological phage descriptions in the year 2000; Arch Virol (2001) 146:843-857; Elizabeth Kutter et al. Bacteriophages biology and application; CRC press).

During infection, a bacteriophage attaches to a bacterium and inserts its genetic material into the cell. After this a bacteriophage follows one of two life cycles, lytic or lysogenic. Lytic bacteriophages take over the machinery of the cell to make phage components. They then destroy or lyse the cell, releasing new phage particles. Lysogenic bacteriophages incorporate their nucleic acid into the chromosome of the host cell and replicate with it as a unit without destroying the cell. Under certain conditions, lysogenic phages can be induced to follow a lytic cycle (Elizabeth Kutter et al. Bacteriophages biology and application. CRC Press).

After the discovery of bacteriophages, a great deal of faith was initially placed in their use for infectious-disease therapy. However, when broad spectrum antibiotics came into common use, bacteriophages were seen as unnecessary due to a specific target spectrum. Nevertheless, the misuse and overuse of antibiotics resulted in rising concerns about antibiotic resistance and harmful effects of residual antibiotics in foods (Cislo, M et al. Bacteriophage treatment of suppurative skin infections. Arch Immunol. Ther. Exp. 1987.2:175-183; Kim sung-hun et al., Bacteriophage; New Alternative Antibiotics. Biological research information center (BRIC)). In particular, antimicrobial growth promoter (AGP), added to animal feed to enhance growth, is known to induce antibiotic resistance, and therefore, the ban of using antimicrobial growth promoter (AGP) has been recently introduced. In the European Union, the use of all antimicrobial growth promoters (AGPs) was banned from 2006. South Korea has banned the use of some AGPs from 2009, and is considering restrictions on the use of all AGPs in the future.

These growing concerns about the use of antibiotics have led to a resurgence of interest in bacteriophage as an alternative to antibiotics. Seven bacteriophages for control of *E. coli* O157:H are disclosed in U.S. Pat. No. 6,485,902 (Use of bacteriophages for control of *Escherichia coli* O157, issued in 2002). Two bacteriophages for control of various microorganisms are disclosed in U.S. Pat. No. 6,942,858 (issued to Nymox in 2005). Many companies have been actively trying to develop various products using bacteriophages. EBI food system (Europe) developed a food additive for preventing food poisoning caused by *Listeria monocytogenes*, named Listex-P100, which is the first bacteriophage product approved by the US FDA. A phage-based product, LMP-102 was also developed as a food additive against *Listeria monocytogenes*, approved as GRAS (Generally Regarded As Safe). In 2007, a phage-based wash produced by OmniLytics was developed to prevent *E. coli* O157 contamination of beef during slaughter, approved by USDA's Food Safety and Inspection Service (FSIS). In Europe, *Clostridium* sporogenes phage NCIMB 30008 and *Clostridium* tyrobutiricum phage NCIMB 30008 were registered as a feed preservative against *Clostridium* contamination of feed in 2003 and 2005, respectively. Such studies show that research into bacteriophages for use as antibiotics against zoonotic pathogens in livestock products is presently ongoing.

However, most of the phage biocontrol studies have focused on the control of *E. coli*, *Listeria*, and *Clostridium*. *Salmonella* is also a zoonotic pathogen, and damages due to this pathogen are not reduced. As mentioned above, since SE and ST exhibit multiple drug resistance, nationwide antimicrobial resistance surveillance has been conducted in South Korea under the Enforcement Decree of the Act on the Prevention of Contagious Disease (Executive Order 16961), Enforcement ordinance of the Act on the Prevention of Contagious Disease (Ministry of Health and Welfare's Order 179), and Organization of the National Institute of Health (Executive Order 17164). Accordingly, there is a need for the development of bacteriophages to control *Salmonella*. The foregoing discussion is solely to provide background information of the invention and do not constitute any admission of prior art.

SUMMARY

One aspect of the present invention relates to an isolated bacteriophage, belonging to the family Siphoviridae of morphotype B1, with a specific bactericidal activity against one or more *Salmonella* bacteria selected from the group consisting of *Salmonella Enteritidis, Salmonella Typhimurium, Salmonella Gallinarum*, and *Salmonella* Pullorum, characterized by one of the following properties: the bacteriophage has a total genome size of 38~45 kb; the bacteriophage contains as a part of the genome thereof at least one nucleic acid sequence selected from among SEQ ID NOS. 1 to 4; and the bacteriophage has structural proteins ranging in size from 37-40 kDa, 62-65 kDa, 51-54 kDa and 10-13 kDa.

According to some embodiments, the foregoing bacteriophage may have a morphological structure composed of an isometric capsid and a long, non-contractile tail.

According to some other embodiments, when PCR is performed in a presence of a primer set selected from among SEQ ID NOS. 5 and 6, SEQ ID NOS. 7 and 8, SEQ ID NOS. 9 and 10, and SEQ ID NOS. 11 and 12, with the genome of the bacteriophage serving as a template, each PCR product may be 500 bp~3 kbp long.

According to still some other embodiments, the foregoing bacteriophage may show at least one of the following properties; tolerance to a range of from pH 3.0 to pH 11.0, tolerance to a heat range of from 37° C. to 70° C., and tolerance to desiccation under a condition of 120° C./70° C.

In one embodiment, the bacteriophage may be identified by accession number KCCM11030P.

Another aspect of the present invention relates to a composition for prevention or treatment of infectious diseases caused by one or more *Salmonella* strains selected from the group consisting of *Salmonella Enteritidis, Salmonella Typhimurium, Salmonella Gallinarum*, and *Salmonella* Pullorum, comprising the foregoing bacteriophage.

In one embodiment, the infectious disease may be salmonellosis and *salmonella* food poisoning when caused by *Salmonella enteritidis* or *Salmonella Typhimurium*, Fowl typhoid when caused by *Salmonella Gallinarum* and pullorum when caused by *Salmonella* Pullorum. In another embodiment, the composition may be used as an antibiotic.

Still another aspect of the present invention relates to an animal feed or drinking water, comprising the foregoing bacteriophage. Still another aspect of the present invention relates to a sanitizer and cleaner, comprising the foregoing bacteriophage.

Still another aspect of the present invention relates to a method for preventing or treating infectious diseases caused by one or more *Salmonella* strains selected from the group consisting of *Salmonella Enteritidis, Salmonella Typhimurium, Salmonella Gallinarum*, and *Salmonella* Pullorum, comprising administering the foregoing bacteriophage to animals in need thereof. In some of certain embodiments, it is related to method for preventing or treating infectious diseases caused by one or more *Salmonella* strains selected from the group consisting of *Salmonella Enteritidis, Salmonella Typhimurium, Salmonella Gallinarum*, and *Salmonella* Pullorum, comprising administering the foregoing composition to animals in need thereof.

DETAILED DESCRIPTION OF THE EMBODIMENTS

Leading to the present invention, intensive and thorough research into bacteriophages, isolated from natural sources, which infect the poultry pathogen *salmonella*, conducted by the present inventors, aiming to overcome problems occurring upon the misuse or overuse of broad spectrum antibiotics, such as the advent of drug or multiple drug resistant bacteria, drug residues, etc., resulted in the finding that some isolated bacteriophages have a specific bactericidal activity against *Salmonella Enteritidis* (SE), *Salmonella Typhimurium* (ST), *Salmonella Gallinarum* (SG) and *Salmonella* Pullorum (SP) with no influences on beneficial bacteria, in addition to showing excellent acid- and heat-resistance and desiccation tolerance, as identified for the morphorlogical, biochemical and genetic properties thereof, and thus that some bacteriophages can be used as active ingredients of compositions for the prevention and treatment of *Salmonella Enteritidis*- or *Salmonella Typhimurium*-mediated diseases, such as livestock salmonellosis and *Salmonella* food poisoning, and *Salmonella Gallinarum*- or *Salmonella* Pullorum-mediated diseases, particularly, Fowl Typhoid and Pullorum disease. Also, bacteriophage according to some embodiments of the present invention can be applied to various products for the control of *Salmonella* bacteria, including livestock feed additives, drinking water for livestock, barn sanitizers, and cleaners for meat products.

It is one aspect of the present invention to provide a novel bacteriophage which has a specific bactericidal activity against one or more *Salmonella* bacteria selected from the group consisting of *Salmonella Enteritidis, Salmonella Typhimurium, Salmonella Gallinarum*, and *Salmonella* Pullorum.

It is another aspect of the present invention to provide a composition for the prevention or treatment of infectious diseases caused by one or more *Salmonella* bacteria selected from the group consisting of *Salmonella Enteritidis, Salmonella Typhimurium, Salmonella Gallinarum*, and *Salmonella* Pullorum, comprising the bacteriophage as an active ingredient.

It is a further aspect of the present invention to provide a livestock feed additive and drinking water for livestock, It is still a further object of the present invention to provide a cleaner or a sanitizer, comprising the bacteriophage as an active ingredient.

It is still another aspect of the present invention to provide a method for preventing or treating salmonellosis or *salmonella* food poisoning caused by *Salmonella Enteritidis* or *Salmonella Typhimurium* using the composition comprising the bacteriophage as an active ingredient. Also, the present invention provides a method for preventing or treating fowl typhoid and pullorum disease caused by *Salmonella Gallinarum* or *Salmonella* Pullorum.

The novel bacteriophage according to some embodiments of the present invention has a specific bactericidal activity against one or more *Salmonella* strain selected from the group consisting of *Salmonella Enteritidis, Salmonella Typhimurium, Salmonella Gallinarum*, and *Salmonella* Pullorum, in addition to showing excellent acid- and heat-resistance and desiccation tolerance. Hence, novel bacteriophages according to some embodiments of the present invention can be used, for the control of *Salmonella Enteritidis, Salmonella Typhimurium, Salmonella Gallinarum*, and *Salmonella* Pullorum as well as for preventing or treating infectious diseases caused by *Salmonella Enteritidis, Salmonella Typhimurium, Salmonella Gallinarum*, or *Salmonella* Pullorum, including salmonellosis, *Salmonella* food poisoning, Fowl Typhoid and Pullorum disease.

DESCRIPTION OF DRAWINGS

FIG. 5 is the result of PCR, performed using each primer set for the ΦCJ7 genomic DNA: A: a primer set of SEQ ID NOS. 5 and 6; B: a primer set of SEQ ID NOS. 7 and 8; C: a primer set of SEQ ID NOS. 9 and 10; and D: a primer set of SEQ ID NOS. 11 and 12. All of the PCR products were 500 bp~3 kbp long;

FIG. 6 is the result of acid-resistance assay on the bacteriophage ΦCJ7, showing the number of surviving bacteriophage at pH 2.1, 2.5, 3.0, 3.5, 4.0, 5.5, 6.4, 6.9, 7.4, 8.0, 9.0, 9.8 and 11.0. The bacteriophage ΦCJ7 did not lose its activity until pH 3.0, but completely lost its activity at pH 2.5 or lower, as compared to control;

Figure 1:
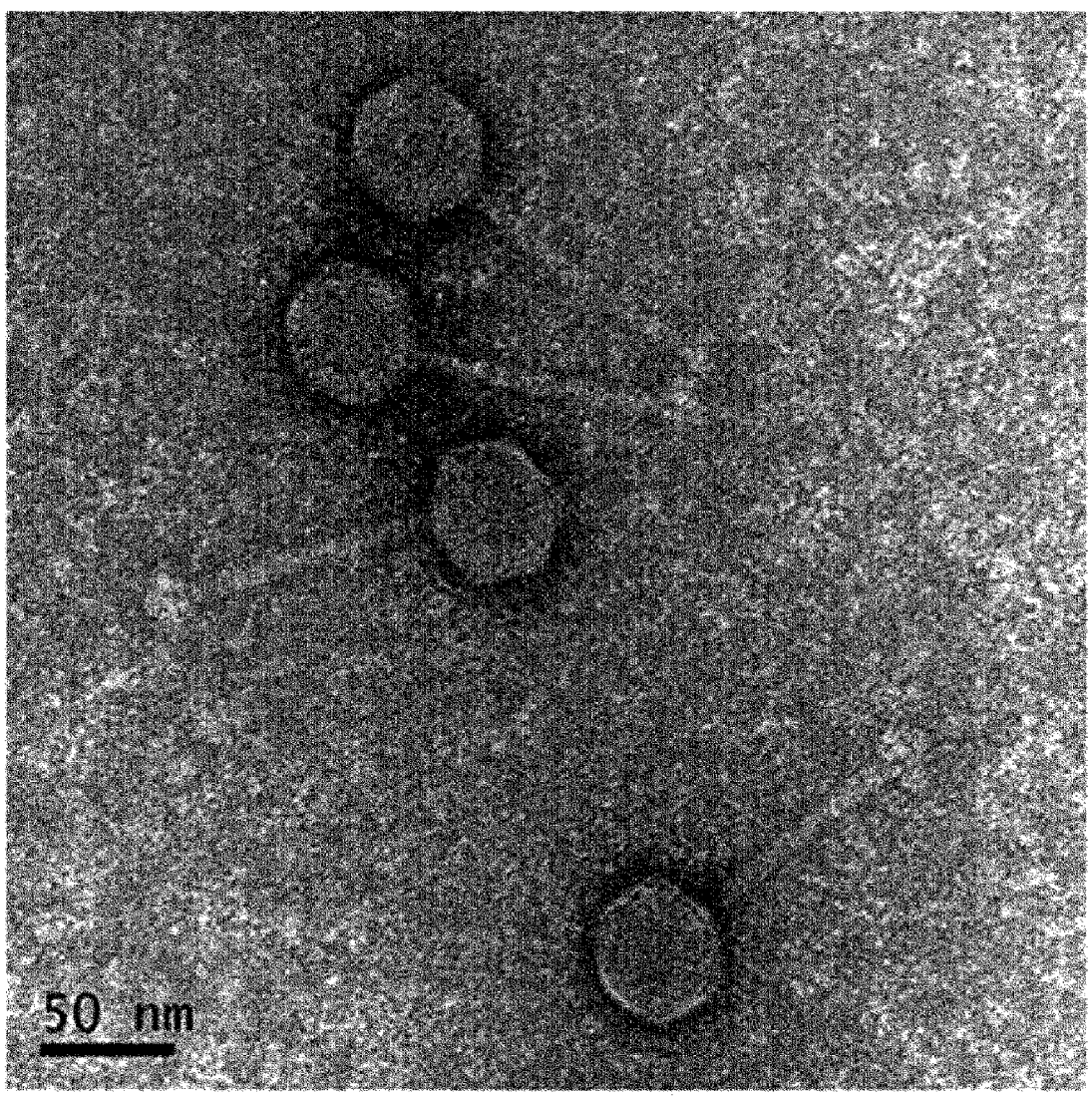
FIG. 1 is an electron microscopy photograph of ΦCJ7, showing that ΦCJ7 belongs to the morphotype group of the family Siphoviridae, characterized by an isometric capsid and a long contractile tail.

One embodiment of the present invention relates to a novel isolated bacteriophage having a specific bactericidal activity against *Salmonella Enteritidis, Salmonella Typhimurium, Salmonella Gallinarum*, or *Salmonella* Pullorum.

The bacteriophage of some embodiments of the present invention belongs to the Siphoviridae family of morphotype B1 with the morphological structure consisting of an isometric capsid and a long, non-contractile tail, having a total genome size of 38~45 kbp and major structural proteins ranging in size from 37 to 40 kDa, from 62 to 65 kDa, from 51 to 54 kDa and from 10 to 13 kDa.

In a preferred embodiment, the bacteriophage according to some embodiments of the present invention shows the species specificity of specifically infecting only *Salmonella Enteritidis, Salmonella Typhimurium, Salmonella Gallinarum*, or *Salmonella* Pullorum. In a preferred embodiment, the bacteriophage of the present invention has a total genome size of approximately 38-45 kbp, and preferably approximately 39.2~44.1 kbp. Further, the bacteriophage may contain as parts of the genome thereof one or more nucleic acid molecules selected from the group consisting of SEQ ID NOS. 1 to 4. Preferably, the bacteriophage contains as parts of the genome thereof nucleic acid molecules consisting of SEQ ID NOS. 1 to 4.

When PCR is performed in the presence of a primer set selected from among SEQ ID NOS. 5 and 6, SEQ ID NOS. 7 and 8, SEQ ID NOS. 9 and 10 and SEQ ID NOS. 11 and 12, with the genome of the bacteriophage according to some embodiments of the present invention serving as a template, each PCR product is 500 bp~3 kbp long. Preferably, When PCR is performed in the presence of above mentioned primer set, respectively, each PCR product is 500 bp~3 kbp long. The term "nucleic acid molecule", as used herein, is intended to include DNA (gDNA and cDNA) and RNA molecules. The term "nucleotides", which when joined together, make up the structural units of nucleic acid molecules, encompass natural ones and sugar- or base-modified analogues thereof.

The bacteriophage according to some embodiments of the present invention has major structural proteins ranging in size from 37 to 40 kDa, from 62 to 65 kDa, from 51 to 54 kDa and from 10 to 13 kDa, and preferably corresponding to respective sizes of approximately 38 kDa, 63 kDa, 52 kDa and 12 kDa.

Further, the bacteriophage according to some embodiments of the present invention shows biochemical properties of being resistant to acid, heat and desiccation.

In greater detail, the bacteriophage according to some embodiments of the present invention has excellent resistance to acid and heat so that it can survive over a wide pH range of from 3.0 to 11.0 and a heat range of from 37° C. to 70° C. With regard to the desiccation tolerance thereof, the bacteriophage can remain viable even under a high temperature and dry condition of 120° C./70° C. Thanks to the superiority thereof in resistance to acid, heat and desiccation, the bacteriophage according to some embodiments of the present invention can be used in a wide range of temperature and pH, finding applications in compositions and products for the prevention and treatment of livestock diseases and livestock-mediated human diseases.

According to one embodiment, a bacteriophage of the present invention which was isolated from a sewage sample of a chicken slaughterhouse that bacteriophage was identified as having a specific bactericidal activity against SG, SP, ST and SE and the above characteristics, and was designated as ΦCJ7 and deposited with the Korean Culture Center of Microorganisms (361-221, Honje 1, Seodaemun, Seoul) on Aug. 14, 2009 under accession number KCCM11030P.

Figure 2:
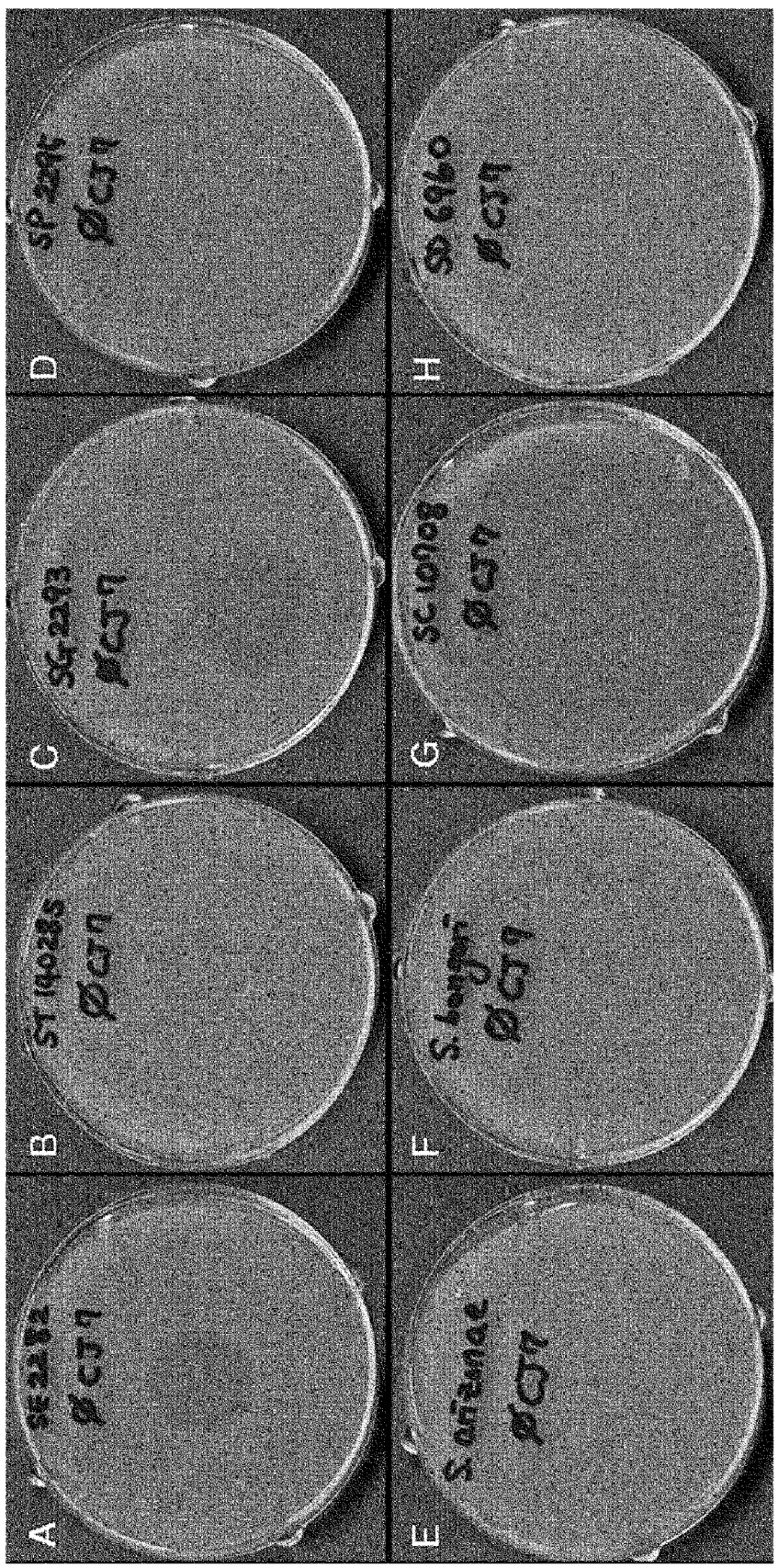
FIG. 2 is of photographs showing the formation of ΦCJ7 plaques in a lawn of *salmonella* bacteria: A: in a lawn of SE; B: in a lawn of ST; C: in a lawn of SG; D: in a lawn of SP; E: in a lawn of SA; F: in a lawn of SB; G: in a lawn of SC; H: in a lawn of SD. Plaques formed in lawns of SE, ST, SG and SP, but not in lawns of SA, SB, SC and SD.

In accordance with an example of the present invention, sewage samples were collected from chicken slaughterhouses and used to isolate therefrom bacteriophages that can lyse the host cell SE. They were also found to lyse SG, SP and ST (FIG. 2 and Table 1). An morphological examination under an electron microscope confirmed that the bacteriophage (ΦCJ7) belongs to the family Siphoviridae of morphotype B1 (FIG. 1).

Figure 3:
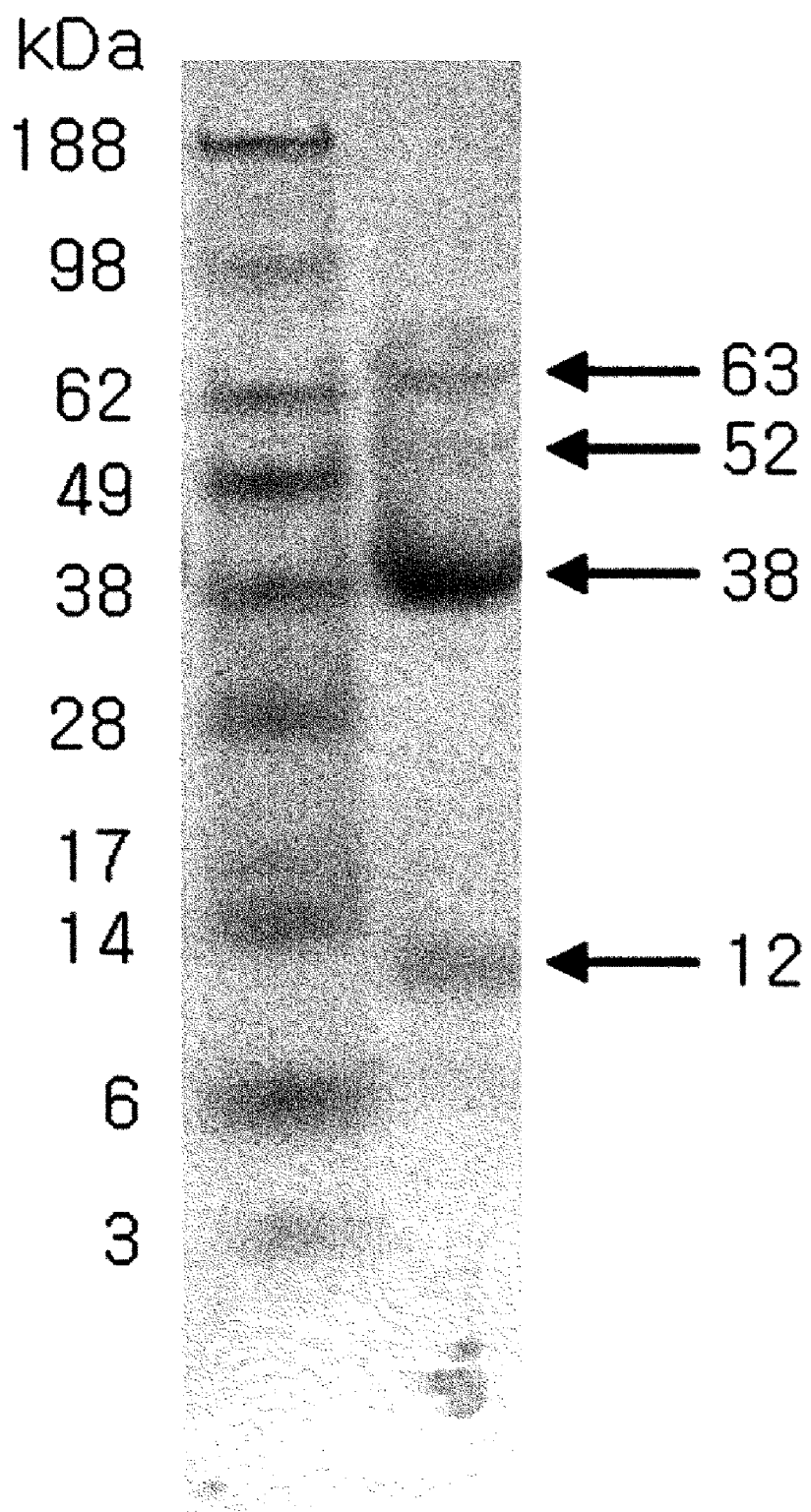
FIG. 3 is the result of SDS-PAGE of the isolated bacteriophage ΦCJ7, in which protein patterns of the bacteriophage are shown, with the appearance of major proteins at 38 kDa, 63 kDa, 52 kDa and 12 kDa (See-blue plus 2 prestained-standard (Invitrogen) used as marker)

The bacteriophage ΦCJ7 was found to have structural proteins of approximately 38 kDa, 63 kDa, 52 kDa and 12 kDa, as measured by a protein pattern analysis (FIG. 3).

Further, a genome analysis showed that ΦCJ7 has a total genome size of approximately 44.1~39.1 kbp (FIG. 4), with the nucleic acid molecules of SEQ ID NOS. 1 to 4 incorporated thereinto (Example 6).

Also, the bacteriophage was found to be of very low genetic similarity with known bacteriophages as measured by the comparison of genetic similarity with other species, indicating that the bacteriophage is a novel one (Table 2). More particularly, when PCR was performed using the primer sets SEQ ID NOS. 5 and 6, SEQ ID NOS. 7 and 8, SEQ ID NOS. 9 and 10, and SEQ ID NOS. 11 and 12, which were designed for ΦCJ7, the resulting PCR products were 500 bp~3 kbp in size (FIG. 5).

Also, the phage plaques (clear zones formed in a lawn of cells on soft agar due to lysis by phage) resulting from the infection of ΦCJ7 into SE, ST, SG and SP were observed to have the same size and turbidity (FIG. 2).

Figure 7:
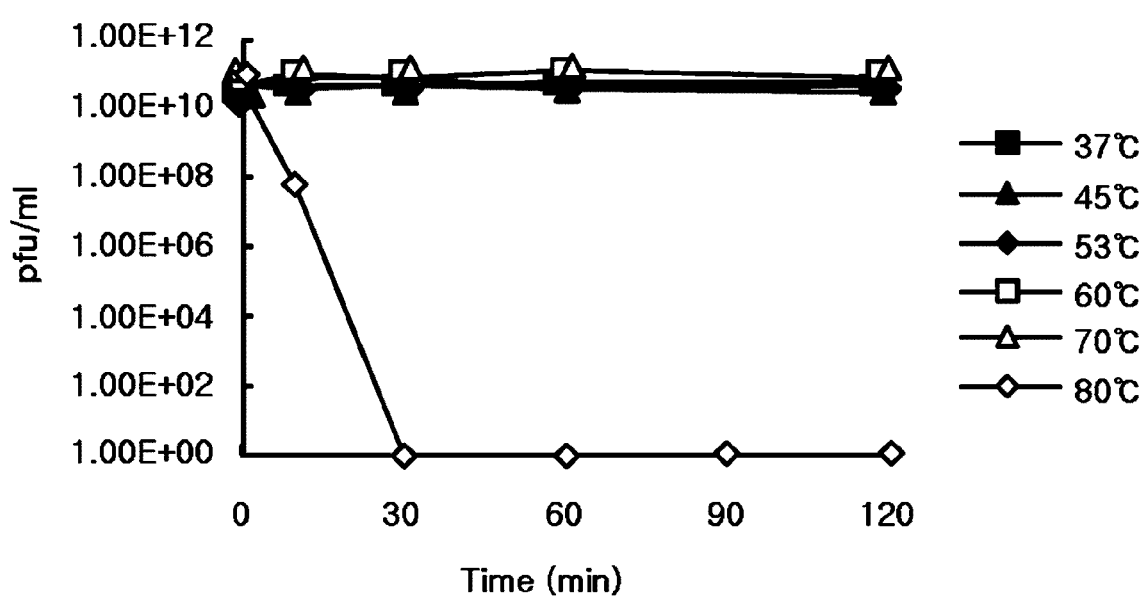
FIG. 7 is the result of heat-resistance assay on the bacteriophage ΦCJ7, showing the number of surviving bacteriophage at 37, 45, 53, 60, 70 and 80° C. for 0, 10, 30, 60 and 120 min. The bacteriophage ΦCJ7 maintained its activity at 70° C. up to 2 hours, lost its activity a little when exposed to 80° C. for 10 mins, completely lost its activity when exposed to more time.
Figure 8:
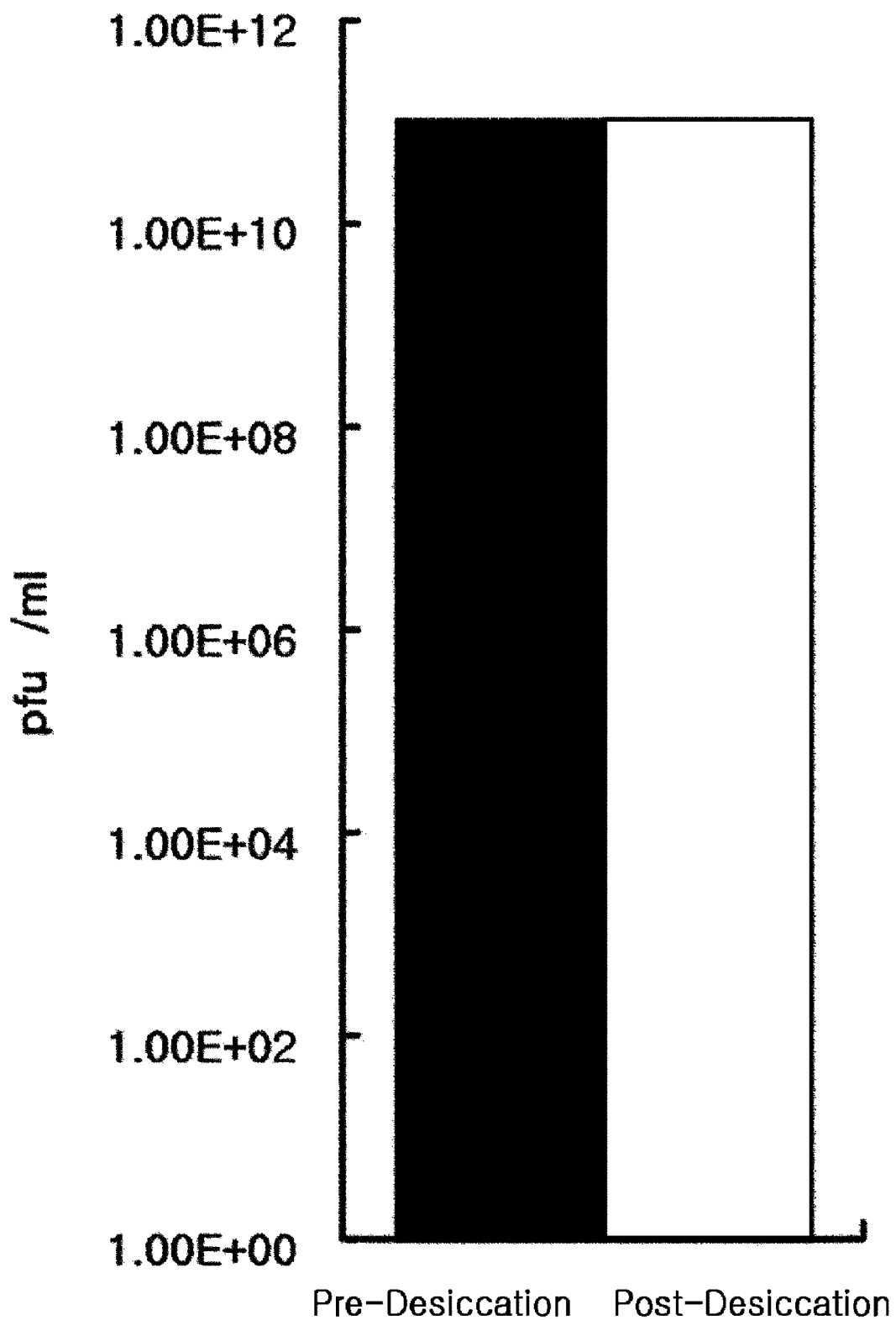
FIG. 8 is the result of desiccation resistance assay on the bacteriophage ΦCJ7 with the aid of a speed-dryer (Lab Plant), in which when titer changes under the dry condition were measured in comparison with pre-drying titers, the activity was 100% maintained.

ΦCJ7 was examined for stability under a wide spectrum of pH, temperature, and desiccation. The bacteriophage was observed to survive over a pH range of from 3.0 to 11.0 (FIG. 6) and a temperature range of from 37° C. to 70° C. (FIG. 7) in addition to remaining stably viable even after desiccation at high temperature (120° C./70° C.) (FIG. 8).

Also, the wild-type strains SE, ST, SG and SP were also found to fall within the host cell range of ΦCJ7 (Table 3). When orally administered with ΦCJ7, rats were observed to remain unchanged in weight (FIG. 9), mortality, general symptoms (Table 4) and organ abnormality (Table 5).

Also, a cleaning assay shows that when used in livestock farms, the bacteriophage ΦCJ7 is found to effectively control *salmonella* (Table 7) and have excellent and consistent bactericidal activity against *salmonella* strains under various conditions, compared to conventional cleaners as positive controls (Table 7).

These data imply that the bacteriophage ΦCJ7 and its mutants can be applied to various products for the control of *salmonella* bacteria.

In accordance with another aspect thereof, the present invention pertains to a composition for the prevention or treatment of infectious diseases caused by one or more *Salmonella* bacteria selected from the group consisting of *Salmonella enteritidis*, *Salmonella Typhimurium*, *Salmonella Gallinarum*, and *Salmonella* Pullorum, comprising the bacteriophage as an active ingredient.

In a preferred embodiment, the composition may contain an antibiotic.

Having specific bactericidal activity against *Salmonella enteritidis*, *Salmonella Typhimurium*, *Salmonella Gallinarum*, and *Salmonella* Pullorum according to some embodiments, the bacteriophage may be used for the purpose of preventing or treating the diseases caused by the bacteria. Preferably, examples of the infectious diseases include salmonellosis and *Salmonella* food poisoning by *Salmonella enteritidis* or *Salmonella Typhimurium*, Fowl Typhoid by *Salmonella Gallinarum* and Pullorum disease by *Salmonella* Pullorum include, but are not limited thereto.

As used herein, the term "samonellosis" refers to symptoms following *salmonella* infection, such as fever, headache, diarrhea, and vomiting. That is, salmonellosis is an infection with bacteria of the genus *Salmonella*, with the accompaniment of two representative symptoms: septicemia such as typhoid fever; and acute gastroenteritis such as food poisoning, enteritis, and acute bacteria.

As used herein, the term "prevention" is intended to encompass all actions for restraining or delaying disease progress through the administration of the composition. The term "treatment" in this context encompasses all actions for improving or beneficially changing the patient's condition through the administration of the composition.

According to some embodiments, the composition comprises ΦCJ7 in an amount of from $5 \times 10^2$ to $5 \times 10^{12}$ pfu/ml, and preferably in an amount of from $1 \times 10^6$ to $1 \times 10^{10}$ pfu/ml.

The composition according to some other embodiments of the present invention may further comprise a pharmaceutically acceptable vehicle, and may be formulated together with the carrier into foods, medicines, and feed additives.

As used herein, the term "pharmaceutically acceptable vehicle" refers to a carrier or diluent that neither causes significant irritation to an organism nor degrades the biological activity and properties of the administered active ingredient. For use in the formulation of the composition into a liquid preparation, a pharmaceutically acceptable vehicle must be suitable for sterilization and biocompatibility. Examples include saline, sterile water, Ringer's solution, buffered physiological saline, albumin infusion solution, dextrose solution, maltodextrin solution, glycerol, and ethanol. They may be used alone or in any combination thereof. If necessary, another conventional additive, such as antioxidants, buffers, bacteriostatic agents, etc., may be added to the composition. When combined additionally with diluents, dispersants, surfactants, binders and/and lubricants, the composition according to some embodiments of the present invention may be formulated into injections such as aqueous solutions, suspensions and emulsions, or pills, capsules, granules, or tablets. The prophylactic or therapeutic compositions according to some embodiments of the present invention may be locally applied to afflicted areas by coating or spraying.

Alternatively, the composition according to some embodiments of the present invention may be administered through oral or parenteral routes. The parenteral routes are available for intravenous, intraperitoneal, intramuscular, subcutaneous or topical administration Depending on a variety of factors including formulations, the mode of administration, the age, weight, sex, condition and diet of the patient or animal being treated, the time of administration, the route of administration, the rate of excretion, and reaction sensitivity, the suitable dosage of the composition according to some embodiments of the present invention will vary when it is applied, sprayed or administered. It will be apparent to those skilled in the art that when the pharmaceutical composition is administered to patients, the suitable total daily dose may be determined by an attending physician or veterinarian within the scope of sound medical judgment.

Oral dosage preparations of the composition according to some embodiments of the present invention may take the form of tablets, troches, lozenges, aqueous or emulsive suspensions, powders or granules, emulsions, hard or soft capsules, syrups, or elixirs. The oral dosage forms such as tablets and capsules may comprise a binder such as lactose, saccharose, sorbitol, mannitol, starch, amylopectin, cellulose or gelatin, an excipient such as dicalcium phosphate, a disintegrant such as corn starch or sweet potato starch, a lubricant such as magnesium stearate, calcium stearate, sodium stearylfumarate, or polyethylene glycol wax. For capsules, a liquid vehicle such as lipid may be further used.

For non-oral administration, the composition according to some embodiments of the present invention may be formulated into injections via subcutaneous, intravenous, or intramuscular routes, suppositories, or sprays inhalable via the respiratory tract, such as aerosols. Injection forms may be prepared by dissolving or suspending the composition of some embodiments of the present invention, together with a stabilizer or a buffer, in water and loading the solution or suspension onto ampules or vial unit forms. For sprays, such as aerosols, a propellant for spraying a water-dispersed concentrate or wetting powder may be used in combination with an additive.

The "antibiotic", as used herein, refer to a substance or compound that can be administered to animals to kill bacteria or inhibit their growth and is intended to encompass antiseptics, bactericidal agents and antibacterial agents. The animals are mammals including humans. Thanks to the advantage of being of higher specificity for *Salmonella* over conventional antibiotics, the bacteriophage according to some embodiments of the present invention can kill the specific pathogens without affecting beneficial bacteria. Furthermore, the bacteriophage according to some embodiments of the present invention does not induce drug resistance so that it can be provided as a novel antibiotic with a long life cycle.

In accordance with a further aspect thereof, the present invention pertains to an animal feed or drinking water, comprising the bacteriophage as an active ingredient.

Feed additive antibiotics used in the fishery and livestock industry are intended to prevent infections. However, most of the currently available feed additive antibiotics are problematic in that they are apt to induce the occurrence of resistant strains and may be transferred to humans as they remain in livestock products. The uptake of such residual antibiotics may make human pathogens resistant to antibiotics, resulting in the spread of diseases. Furthermore, many kinds of feed additive antibiotics, usually used in combination in animal feeds, may cause the emergence of multidrug-resistant strains. Therefore, the bacteriophage according to some embodiments of the present invention can be used as a feed additive antibiotic that is eco-friendly enough to be a solution to the problems.

The animal feed according to some embodiments of the present invention may be prepared by adding the bacteriophage directly or in a separate feed additive form to an animal feed. In an animal feed, the bacteriophage according to some embodiments of the present invention may take a liquid or a dry form, and preferably exist as a dried powder. In this regard, the bacteriophage according to some embodiments of the present invention may be dried by air drying, natural drying, spray drying or freeze-drying, but these drying processes do not limit the present invention. The bacteriophage according to some other of embodiments of the present invention may be added as powder in an amount of from 0.05 to 10% by weight, preferably in an amount of from 0.1 to 2% by weight, based on the total weight of animal feed. The animal feed may comprise other conventional additives useful for the preservation thereof for a long term, in addition to the bacteriophage of some embodiments of the present invention.

To the feed additive according to some embodiments of the present invention may be added another non-pathogenic microorganism. The available additional microorganism may be selected from the group consisting of *Bacillus subtilis* that can produce protease, lipase and invertase, *Lactobacillus* sp. strain that can exert physiological activity and a function of decomposing under anaerobic conditions, such as in the stomach of cattle, filamentous fungi including *Aspergillus oryzae* (J Animal Sci 43:910-926, 1976) that increases the weight of domestic animals, enhances milk production and helps the digestion and absorptiveness of feeds, and yeast including *Saccharomyce scerevisiae* (J Anim Sci56:735-739, 1983).

The animal feed comprising ΦCJ7 in accordance with some embodiments of the present invention may include plant-based feeds, such as grains, nuts, food byproducts, seaweed, fiber, drug byproducts, oil, starches, meal, and grain byproducts, and animal-based feeds such as proteins, minerals, fat, single cell proteins, zooplankton, and food wastes, but is not limited thereto.

The feed additive comprising ΦCJ7 in accordance with some other embodiments the present invention may include additives for preventing quality deterioration, such as binders, emulsifiers and preservatives, and additives for increasing utility, such as amino acids, vitamins, enzymes, probiotics, flavorings, non-protein nitrogen, silicates, buffering agents, coloring agents, extracts, and oligosaccharides, but is not limited thereto.

When supplied with drinking water containing the bacteriophage according to some embodiments of the present invention, livestock can be continuously reduced in the population of *Salmonella* bacteria in the intestine thereof livestock. As a result, *Salmonella*-free livestock can be produced.

In accordance with still a further aspect thereof, the present invention pertains to a cleaner or a sanitizer, comprising the bacteriophage as an active ingredient.

The sanitizer comprising the bacteriophage as an active ingredient is very useful for food hygiene against, for example, food poisoning. In detail, the sanitizer may be utilized not only as an agent or a food additive for preventing *salmonella* contamination, but also in the production of *salmonella*-free livestock. In order to remove *Salmonella*, the sanitizer can also be sprayed over domestic sewages and applied to poultry barns, slaughterhouses, spots where livestock died, cooking spaces and cooking facilities, and any area where poultry acts.

Further, the cleaner comprising the bacteriophage as an active ingredient can be used on a body area of living animals, such as skin, feathers and the like, which is already or potentially contaminated with *Salmonella* bacteria.

In accordance with still another aspect, the present invention pertains to a method for the prevention or treatment of *Salmonella* Enteritidis-*Salmonella* Typhimurium-, *Salmonella* Gallinarum-, or *Salmonella* Pullorum-mediated infectious diseases, comprising administering to an animal in need thereof a bacteriophage having a specific bactericidal activity against *Salmonella Enteritidis*, *Salmonella Typhimurium*, *Salmonella Gallinarum*, or *Salmonella* Pullorum.

In accordance with yet another aspect thereof, the present invention pertains to a method for the prevention or treatment of *Salmonella Enteritidis*-*Salmonella Typhimurium*-, *Salmonella Gallinarum*-, or *Salmonella* Pullorum-mediated infectious diseases, comprising administering to an animal in need thereof a composition for the prevention or treatment of *Salmonella Enteritidis*-, *Salmonella Typhimurium*-, *Salmonella Gallinarum*-, or *Salmonella* Pullorum-mediated diseases.

The composition according to some embodiments of the present invention may be administered in the form of a pharmaceutical formulation into animals or may be ingested as a mixture with animal feed or drinking water by animals and preferably as a mixture with animal feed. In the present invention, the animals include cattle, pigs, chicken, poultry and humans, but are not limited thereto. As long as it reaches target tissues, any route, whether oral or parenteral, may be taken for administering the composition of some embodiments of the present invention. In detail, the composition of some other embodiments of the present invention may be administered via oral, rectal, topical, intravenous, intraperitoneal, intramuscular, intraarterial, transdermal, intranasal, and inhalation routes.

The method for the treatment of diseases in accordance with some embodiments of the present invention comprises administering the composition according to some of certain embodiments of the present invention in a therapeutically effective amount. It is apparent to those skilled in the art that the total daily dose should be determined by an attending physician or veterinarian within the scope of sound medical judgment. The therapeutically effective amount for a given patient may vary depending on various factors well known in the medical art, including the kind and degree of the response to be achieved, the patient's age, body weight, state of health, sex, and diet, time and route of administration, the secretion rate of the composition, the time period of therapy, concrete compositions according to whether other agents are used therewith or not, etc.

A better understanding of some embodiments of the present invention may be obtained through the following examples which are set forth to illustrate, but are not to be construed as limiting the present invention.

Example 1

*Salmonella* Bacteriophage Isolation 1-1. Bacteriophage Screening and Single Bacteriophage Isolation 50 ml of each sample from a chicken slaughterhouse and a nearby sewage disposal plant was transferred to a centrifuge tube, and centrifuged at 4000 rpm for 10 min, followed by filtering the supernatant through a 0.45 μm filter. 18 mL of the sample filtrate was mixed with 150 μl of a *Salmonella Enteritidis* (hereinafter referred to as "SE") shaking culture medium ($OD_{600}$=2) and 2 mL of 10× Luria-Bertani medium (hereinafter referred to as "LB medium") tryptone 10 g; yeast extract 5 g; NaCl 10 g; in a final volume of 1 L). The mixture was cultured at 37° C. for 18 hrs and then centrifuged at 4000 rpm for 10 min after which the supernatant was filtered through a 0.2 μm filter. Separately, a mixture of 3 ml of 0.7% agar (w/v) and 150 μl of the SE shaking culture medium ($OD_{600}$=2) was poured across an LB plate and allowed to solidify. Over this plate was spread 10 μl of the culture filtrate, followed by incubation for 18 hrs at 37° C. (0.7% agar was used as "top-agar" and the titration of phage lysate was performed on the top-agar, called soft agar overlay technique). A dilution of the sample culture medium containing the phage lysate was mixed with 150 μL of an SE shaking culture medium ($OD_{600}$=2) and subjected to soft agar overlay assay to produce single plaques. Since a single plaque consisted of the same bacteriophage, one plaque was taken and dissolved in 400 μL of an SM solution (NaCl, 5.8 g; $MgSO_4 7H_2$ 0.2 g; 1M Tris-Cl (pH 7.5), 50 mL; $H_2O$, in a final volume of 1 L), and left for 4 hrs at room temperature to isolate single bacteriophages. To amplify the isolated bacteriophage, 100 μL of the supernatant was taken from the single bacteriophage solution, mixed with 12 mL of 0.7% agar and 500 μL of an SE shaking culture medium, and subjected to a soft agar overlay assay on an LB plate (150 mm in diameter). 15 mL of an SM solution was poured to a plate in which lysis had been completed, after which the plate was gently shaken for 4 hrs at room temperature to elute the bacteriophages from the top-agar. The SM solution containing the eluted bacteriophages was recovered, and chloroform was added in an amount corresponding to 1% of the final volume, and mixed well for 10 min. After centrifugation at 4000 rpm for 10 minutes, the resulting supernatant was filtered through a 0.2 μm filter, and stored in the refrigerator until use.

1-2. Large-Scale Batches of Bacteriophage

The selected bacteriophage was cultured at a large scale using SE. SE was cultured with shaking. After an aliquot of $1.5×10^{10}$ cfu (colony forming units) was centrifuged at 4000 rpm for 10 min, the pellet was re-suspended in 4 mL of an SM solution. Into the suspension was inoculated $7.5×10^7$ pfu (plaque forming unit) of the bacteriophage at an MOI (multiplicity of infection) of 0.005), followed by incubation at 37° C. for 20 min. This solution was inoculated into 150 mL of an LB media in a flask, and cultured at 37° C. for 5 hrs. Chloroform was added in an amount corresponding to 1% of the final volume before the culture solution was shaken for 20 min. DNase I and RNase A were added to a final concentration of 1 μg/ml, each. The solution was left at 37° C. for 30 min. NaCl and PEG (polyethylene glycol) were added to a final concentration of 1 M and 10% (w/v), respectively and left at 4° C. for an additional 3 hrs. The solution was centrifuged at 4° C. and 12,000 rpm for 20 min to discard the supernatant. A suspension of the pellet in 5 mL of an SM solution was left at room temperature for 20 minutes and mixed well with 4 mL of chloroform. After centrifugation at 4° C. and 4000 rpm for 20 min, the supernatant was filtered through a 0.2 μm filter and then subjected to ultracentrifugation using a glycerol density gradient to purify ΦCJ7 (density: 40%, 5% glycerol at 35,000 rpm and 4° C. for 1 hr). The purified ΦCJ7 was re-suspended in 300 μL of an SM solution, followed by titration. ΦCJ7 was deposited with the Korean Culture Center of Microorganisms (361-221, Honje 1, Seodaemun, Seoul) on Aug. 14, 2009 under accession number KCCM11030P.

Example 2

Examination on ΦCJ7 Infection of *Salmonella*

To analyze the selected bacteriophage for lytic activity on *Salmonella* species other than SE, attempts were made of cross infection with other *Salmonella* species. As a result, ΦCJ7 did not infect SC (*Salmonella* Choleraesuis), SD (*Salmonella* Derby), SA (*Salmonella arizonae*), and SB (*Salmonella bongori*), but infected SE (*Salmonella Enteritidis*), ST (*Salmonella Typhimurium*), SG (*Salmonella Gallinarum*) and SP (Salmonella Pullorum) (see Example 11). The results are summarized in Table 1, below and shown in FIG. 2.

TABLE 1

ΦCJ7 Infection of *Salmonella*

| Serotype | Strain name | Plaque formation |
|---|---|---|
| SE | SGSC 2282 | ○ |
| ST | ATCC 14028 | ○ |
| SG | SGSC 2293 | ○ |
| SP | SGSC 2295 | ○ |
| SA | ATCC 13314 | X |
| SB | ATCC 43975 | X |
| SC | ATCC 10708 | X |
| SD | ATCC 6960 | X |

ATCC: The Global Bioresource Center
SGSC: *Salmonella* Genetic Stock Center

Example 3

Morphology of Bacteriophage ΦCJ7

The purified ΦCJ7 was diluted in a 0.01% gelatin solution, and then fixed in a 2.5% glutaraldehyde solution. The sample was dropped onto a carbon-coated mica plate (ca.2.5×2.5 mm), adapted for 10 min, and washed with sterile distilled water. A carbon film was mounted on a copper grid, stained with 4% uranyl acetate for 30-60 sec, and dried. Examination under a JEM-1011 transmission electron microscope (at 80 kV, magnification of ×120,000~×200,000), as shown in FIG. 1, had it that the purified ΦCJ7 consisted morphologically of an isometric capsid and a long non-contractile tail, indicating that it belongs to the family Siphoviridae of morphotype B1.

Example 4

Protein Pattern Analysis of ΦCJ7

15 μL of a ΦCJ7 solution purified at a titer of $10^{12}$ pfu/ml was mixed with 3 μL of a 5×SDS sample solution, and heated for 5 min. The total protein of ΦCJ7 was run on 4~12% NuPAGE Bis-Tris gel (Invitrogen). Then, the gel was stained with Coomassie blue for 1 hr at room temperature. Major bands were detected at approximately 38 kDa, 63 kDa, 52 kDa and 12 kDa, as shown in FIG. 3.

Example 5

Total Genomic DNA Size of ΦCJ7

Figure 4:
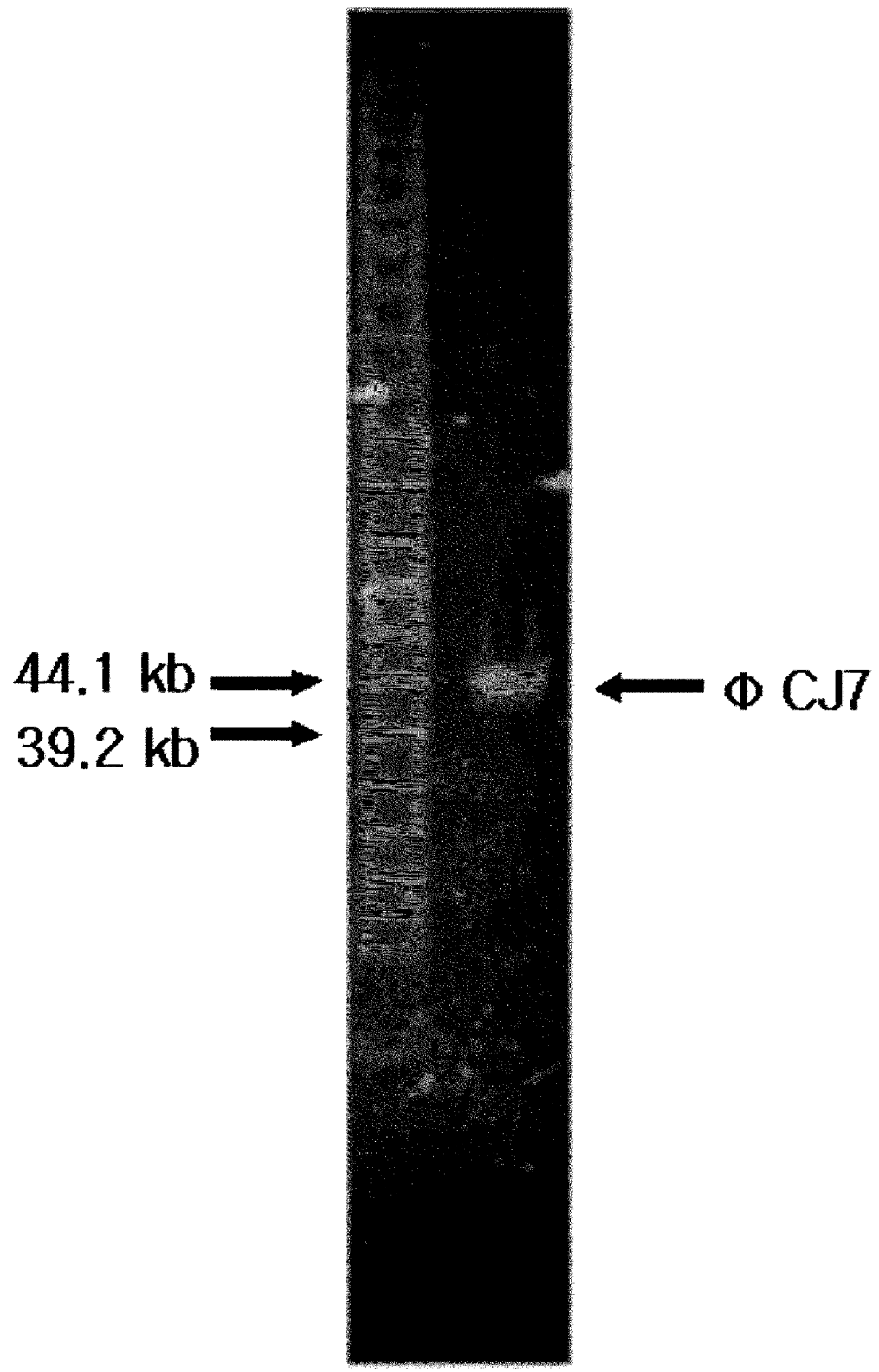
FIG. 4 is the result of PFGE of the isolated bacteriophage ΦCJ7, showing the total genome size of from approximately 39.2 to 44.1 kbp, with a 5 kbp DNA size standard (Bio-rad) serving as a size marker.

Genomic DNA of ΦCJ7 was isolated using ultracentrifugation. In this regard, to a purified ΦCJ7 culture medium were added EDTA (ethylenediaminetetraacetic acid (pH 8.0)), proteinase K, and SDS (sodium dodecyl sulfate) at a final concentration of 20 mM, 50 ug/ml, and 0.5% (w/v), respectively, followed by incubation at 50° C. for 1 hr. An equal volume of phenol (pH 8.0) was added and mixed well. After centrifugation at 12,000 rpm and room temperature for 10 min, the supernatant was mixed well with an equal volume of PCI (phenol:chloroform:isoamylalhocol=25:24:1). Another centrifugation at 12,000 rpm and room temperature for 10 min produced a supernatant which was then mixed with 1/10 volume of 3 M sodium acetate and two volumes of cold 95% ethanol, and left at −20° C. for 1 hr. After centrifugation at 0° C. and 12,000 rpm for 10 min, the supernatant was completely removed, and the DNA pellet was dissolved in 50 μL of TE (Tris-EDTA (pH 8.0)). The extracted DNA was diluted 10-fold, and measured for absorbance at $OD_{260}$ to determine its concentration. 1 μg of the total genomic DNA was loaded onto 1% PFGE (pulse-field gelelectrophoresis) agarose gel and electrophoresed at room temperature for 20 hrs with the aid of a BIO RAD PFGE system program 7 (size range 25-100 kbp; switch timer amp 0.4-2.0 seconds, linear shape; forward voltage 180 V; reverse voltage 120 V). As shown in FIG. 4, the genomic DNA of ΦCJ7 was approximately 39.2-44.1 kb long.

Example 6

Genetic Analysis of ΦCJ7

The genetic analysis of the purified ΦCJ7 started with double digesting 5 μg of the genomic DNA of ΦCJ7 with the restriction enzymes StuI and NruI, AfeI and HinCII, and SnaBI and PvuII. The vector pCL1920 (Promega) was digested with Sma I, and treated with CIP (calf intestinal alkaline phosphatase). A T-blunt vector (Sogent) was also employed. The digested genomic DNA was mixed at a ratio of 3:1 with the vector, and ligated at 16° C. for 2 hrs. The resulting recombinant vector was transformed into *E. coli* DH5a which was then plated on an LB plate containing specinomycin or kanamycin and X-gal (5-bromo-4-chloro-3-indolyl-beta-D-galactopyranoside) for blue/white selection. The selected colonies were cultured for 16 hrs in a culture medium containing the antibiotic with shaking. Then, plasmids were extracted using a plasmid purification kit (Promega). The cloning of the plasmids was confirmed by PCR using primer sets of FRT135 and FRT136 (SEQ ID NOS. 13 and 14) and M13 forward and M13 reverse (SEQ ID NOS. 15 and 16), and selection was made only of insert fragments having a size of 1 kb or longer. Their base sequences were analyzed using the primer sets. The base sequences thus obtained were given in SEQ ID NOS. 1 to 4, respectively, each being 500 bp~3 kbp long, and analyzed for sequence similarity with the aid of a NCBI blastx program, and the results are summarized in Table 2, below.

TABLE 2

Sequence Similarity between ΦCJ7 and Other Bacteriophages

| No | Organism | Protein | Blastx | | | |
| | | | Query | Subject | Identity | e-value |
|---|---|---|---|---|---|---|
| 1 | *Salmonella* phage KS7 | hypothetical protein | 118-567 | 17-166 | 146/150 (97%) | 6e−84 |
| | *Salmonella* phage SETP3 | enolase-like protein | 567-1031 | 1-155 | 145/155 (93%) | 5e−76 |
| | Bacteriophage MB78 | hypothetical protein | 659-297 | 1-120 | 113/121 (93%) | 2e−60 |

TABLE 2-continued

Sequence Similarity between ΦCJ7 and Other Bacteriophages

| | | | Blastx | | | |
|---|---|---|---|---|---|---|
| No | Organism | Protein | Query | Subject | Identity | e-value |
| 2 | *Salmonella* phage SETP3 | hypothetical protein | 618-472 | 75-123 | 40/49 (81%) | 8e−31 |
| | Enterobacteria phage T1 | putative endinuclase | 108-479 | 261-384 | 123/124 (99%) | 5e−60 |
| | *Erwinia* phage Era103 | hypothetical protein | 498-119 | 1-119 | 69/119 (57%) | 1e−31 |
| 3 | *Escherichia coli* | hypoxanthine phosphoribosyltransferase | 489-268 | 109-182 | 73/74 (98%) | 1e−33 |
| | *Shigella flexneri* | hypoxanthine-guanine phosphoribosyltransferase | 285-506 | 126-199 | 73/74 (98%) | 1e−65 |
| 4 | *Salmonella* phage KS7 | hypothetical protein | 103-1131 1128-25 | 3-346 212-581 | 349/371 (94%) 161/166 (96%) | 0e−00 3e−93 |

Example 7

Design of ΦCJ7-Specific Primer Sequences

In order to identify ΦCJ7, ΦCJ7-specific primers were designed on the basis of SEQ ID NOS. 1 to 4. PCR was performed using each primer set of SEQ ID NOS. 5 and 6, SEQ ID NOS. 7 and 8, SEQ ID NOS. 9 and 10, and SEQ ID NOS. 11 and 12. 0.1 μg of the genomic DNA of bacteriophage and 0.5 pmol of each primer were added to a pre-mix (Bioneer), and the final volume was adjusted to 20 μL. PCR was performed with 30 cycles of denaturation; 94° C. 30 sec, annealing; 60° C. 30 sec, and polymerization; 72° C., 1.5 min. The PCR products thus obtained were approximately 500 bp~3 kbp long, with the primer sets of SEQ ID NOS. 5 and 6, SEQ ID NOS. 7 and 8, SEQ ID NOS. 9 and 10, and SEQ ID NOS. 11 and 12. The results are shown in FIG. 5.

Example 8 pH Stability of Bacteriophage

In order to determine whether ΦCJ7 survives the low pH environment in the stomach of chicken, ΦCJ7 was assayed for stability in a wide range of pH (pH 2.1, 2.5, 3.0, 3.5, 4.0, 5.5, 6.4, 6.9, 7.4, 8.2, 9.0, 9.8, and 11.0). Various pH solutions (sodium acetate buffer (pH 4.0, pH 5.5, and pH 6.4), sodium citrate buffer (pH 2.5, pH 3.0, and pH 3.5), sodium phosphate buffer (pH 6.9 and pH 7.4) and Tris-HCl (pH 8.2, pH 9.0, pH 10.0 and pH 11.0)) were prepared to have a concentration of 0.2 M. 180 μL of each pH solution was mixed with 20 μL of a bacteriophage solution ($1.0 \times 10^{11}$ pfu/ml) to give each pH solution a concentration of 1M, followed by incubation at room temperature for 2 hrs. The reaction solution was serially diluted, and 10 μL of each dilution was cultured at 37° C. for 18 hrs by a soft agar overlay method to determine the titers of the phage lysates. Titer changes with pH were measured to determine the stability of bactriophage over pH in comparison to titers of ΦCJ7 at 0 hr. The results showed that the bacteriophage did not lose its activity and remained stable down to pH 3.0. However, it lost its activity at pH 2.5 or lower. The results are shown in FIG. 6.

Example 9

Heat Stability of Bacteriophage

For use as a feed additive, the bacteriophage was assayed for stability to the heat generated during a formulation process. In this regard, 200 μL of a ΦCJ7 solution with a titer of $1.0 \times 10^{11}$ pfu/ml was incubated at 37° C., 45° C., 53° C., 60° C., 70° C., or 80° C. for 0 min, 10 min, 30 min, 60 min and 120 min. The solution was serially diluted, and 10 μL of each dilution was cultured at 37° C. for 18 hrs by a soft agar overlay method to determine the titers of phage lysates. Titer changes with temperature and exposure time were measured to determine the stability of bacteriophage to heat in comparison to titers at 0 hr and 37° C. The results showed that the bacteriophage did not lose its activity at 70° C. up to 2 hrs, lost its activity a little when exposed to 80° C. for 10 min, but completely lost its activity when exposed to 80° C. for more than 10 min. The results are shown in FIG. 7.

Example 10

Desiccation Tolerance of Bacteriophage

For use as a feed additive, the bacteriophage was assayed for tolerance to the dry condition set for a formulation process. On the basis of the results obtained from the heat stability assay, a desiccation assay was performed using a spray-dryer (Lab Plant). Dextrin and sugar, both serving as stabilizers, were added in an amount of 40% and 2% (w/v), respectively, to 50 mL of a ΦCJ7 solution having a titer of $1.0 \times 10^{11}$ pfu/ml. The resulting solution was sprayed inside a spray-dryer in which the inlet and the outlet were maintained at 120° C. and 70° C., respectively. 0.3 g of the powder thus obtained was re-suspended in 2 mL of an SM solution and measured for titer values. After desiccation, the bacteriophage was not decreased in activity at all, compared to pre-drying titers. The results are shown in FIG. 8.

Example 11

Spectrum of Wile-Type Host Cell Strains to Which Bacteriophage Infects

ΦCJ7 was assayed for lytic activity against Korean wild-type *Salmonella Enteritidis* (36 strains), *Salmonella Typhimurium* (22 strains), *Salmonella Gallinarum* (56 strains), *Salmonella* Pullorum (19 strains), *Salmonella* Choleraesuis (2 strains), *Salmonella* Derby (4 strains) and *Salmonella* Arizona (1 strain), and *Salmonella* Bongori (1 strain), obtained from Laboratory of Avian Diseases, College of Veterinary Medicine, Seoul National University, and National Veterinary Research and Quarantine Service and the Korea Centers for Disease Control and Prevention, in addition to the strains used in at least some embodiments of the present invention, SE (SGSC SE2282), ST (ATCC ST14028), SG (SGSC SG2293), and SP (SGSC SP2295). 150 μL of each strain shaking culture medium ($OD_{600}=2$) was mixed, and 10 μL of ΦCJ7 solution ($10^{10}$ pfu/ml) was cultured at 37° C. for 18 hrs using a soft agar overlay method to monitor the formation of plaques. It was observed that the bacteriophage ΦCJ7 showed lytic activity of 94% against all SE, ST, SG and SP. The results are summarized in Table 3, below.

TABLE 3

Lytic Activity of ΦCJ7 against Korean Wild-Type Strains SE, ST, SG, and SP

| Serotype | Strain name | ΦCJ7 Plaque Formation |
|---|---|---|
| SG | SNU SG1 | ○ |
|  | SNU SG2 | ○ |
|  | SNU SG3 | ○ |
|  | SNU SG4 | ○ |
|  | SNU SG5 | ○ |
|  | SNU SG6 | ○ |
|  | SNU SG7 | ○ |
|  | SNU SG8 | ○ |
|  | SNU SG9 | ○ |
|  | SNU SG10 | ○ |
|  | SNU SG11 | ○ |
|  | SNU SG12 | ○ |
|  | SNU SG13 | ○ |
|  | SNU SG14 | ○ |
|  | SNU SG15 | ○ |
|  | SNU SG16 | ○ |
|  | SNU SG17 | ○ |
|  | SNU SG18 | ○ |
|  | SNU SG19 | ○ |
|  | SNU SG20 | ○ |
|  | SNU SG21 | ○ |
|  | SNU SG22 | ○ |
|  | SNU SG23 | ○ |
|  | SNU SG24 | ○ |
|  | SNU SG25 | ○ |
|  | SNU SG26 | ○ |
|  | SNU SG27 | ○ |
|  | SNU SG28 | ○ |
|  | SNU SG30 | ○ |
|  | SNU SG31 | ○ |
|  | SNU SG32 | ○ |
|  | SNU SG33 | ○ |
|  | SNU SG34 | ○ |
|  | SNU SG36 | ○ |
|  | SNU SG37 | ○ |
|  | SNU SG38 | ○ |
|  | SNU SG39 | ○ |
|  | SNU SG40 | ○ |
|  | SNU SG41 | ○ |
|  | SNU SG42 | ○ |
|  | SNU SG43 | ○ |
|  | SNU SG44 | ○ |
|  | SNU SG45 | ○ |
|  | SNU SG46 | ○ |
|  | SNU SG47 | ○ |
|  | SNU SG48 | ○ |
|  | SNU SG49 | ○ |
|  | SNU SG50 | ○ |
|  | SGSC SG9184 | ○ |
|  | SGSC SG2292 | ○ |
|  | SGSC SG2293 | ○ |
|  | SGSC SG2744 | ○ |
|  | SGSC SG2796 | ○ |
| SP | SNU SP1 | ○ |
|  | SNU SP4 | ○ |
|  | SNU SP5 | ○ |
|  | SNU SP8 | ○ |
|  | SNU SP11 | ○ |
|  | SGSC SP2294 | ○ |
|  | SGSC SP2295 | ○ |
|  | SGSC SP2737 | ○ |
|  | SGSC SP2739 | ○ |
|  | SGSC SP2742 | ○ |
|  | SGSC SP2743 | ○ |
|  | SGSC SP2745 | ○ |
|  | SGSC SP2751 | ○ |
|  | SGSC SP4663 | ○ |
|  | SGSC SP4664 | ○ |
|  | SGSC SP4665 | ○ |
|  | SGSC SP4666 | ○ |
|  | SGSC SP4667 | ○ |
|  | SGSC SA1684 | ○ |
| ST | SNU ST1 | ○ |
|  | SNU ST2 | ○ |
|  | SNU ST3 | ○ |
|  | SNU ST4 | ○ |
|  | SNU ST7 | ○ |
|  | SNU ST8 | ○ |
|  | SNU ST11 | ○ |
|  | SNU ST12 | ○ |
|  | SNU ST13 | X |
|  | SNU ST14 | ○ |
|  | SNU ST17 | ○ |
|  | SNU ST18 | ○ |
|  | SNU ST19 | X |
|  | SNU ST20 | ○ |
|  | SNU ST25 | ○ |
|  | SNU ST26 | ○ |
|  | SNU ST37 | ○ |
|  | SNU ST38 | ○ |
|  | SNU ST41 | ○ |
|  | SNU ST42 | ○ |
|  | ATCC UK1 | ○ |
|  | ATCC 14028S | ○ |
|  | SGSC STM1412 | ○ |
|  | SGSC STM260 | ○ |
|  | SGSC STM SA2197 | ○ |
| SE | SGSC SE2282 | ○ |
|  | SGSC SE2377 | ○ |
|  | PT4 S1400194 | ○ |
|  | PT4 LA52 | ○ |
|  | NVRQS SE004 | ○ |
|  | NVRQS SE005 | ○ |
|  | KCDC SE008 | ○ |
|  | KCDC SE009 | ○ |
|  | KCDC SE010 | ○ |
|  | KCDC SE011 | ○ |
|  | KCDC SE012 | ○ |
|  | KCDC SE013 | ○ |
|  | KCDC SE014 | ○ |
|  | KCDC SE015 | ○ |
|  | KCDC SE016 | ○ |
|  | KCDC SE017 | ○ |
|  | KCDC SE018 | ○ |
|  | KCDC SE019 | ○ |
|  | KCDC SE020 | ○ |
|  | KCDC SE021 | ○ |
|  | KCDC SE022 | ○ |
|  | KCDC SE023 | ○ |
|  | KCDC SE024 | ○ |
|  | KCDC SE025 | ○ |
|  | KCDC SE026 | ○ |
|  | KCDC SE027 | ○ |
|  | KCDC SE028 | ○ |
|  | KCDC SE029 | ○ |
|  | KCDC SE030 | ○ |
|  | KCDC SE031 | ○ |
|  | KCDC SE032 | ○ |
|  | KCDC SE033 | ○ |
|  | KCDC SE034 | ○ |
|  | KCDC SE035 | ○ |
|  | KCDC SE036 | ○ |
|  | KCDC SE037 | ○ |

TABLE 3-continued

Lytic Activity of ΦCJ7 against Korean
Wild-Type Strains SE, ST, SG, and SP

| Serotype | Strain name | ΦCJ7 Plaque Formation |
|---|---|---|
| SC | ATCC SC10708 | X |
|  | ATCC SC2929 | X |
| SD | ATCC SD6960 | X |
|  | ATCC SD2466 | ○ |
|  | ATCC SD2467 | ○ |
|  | ATCC SD2468 | X |
| SA | ATCC SA13314 | X |
| SB | ATCC SB43975 | X |

SNU: Laboratory of Avian Diseases, College of Veterinary Medicine, Seoul National University
SGSC: *salmonella* genetic stock center
NVRQS: National Veterinary Research & Quarantine Service
KCDC: Korean Centers for Disease Control and prevention Example 12

Toxicity Assay of Bacteriophage

Figure 9:
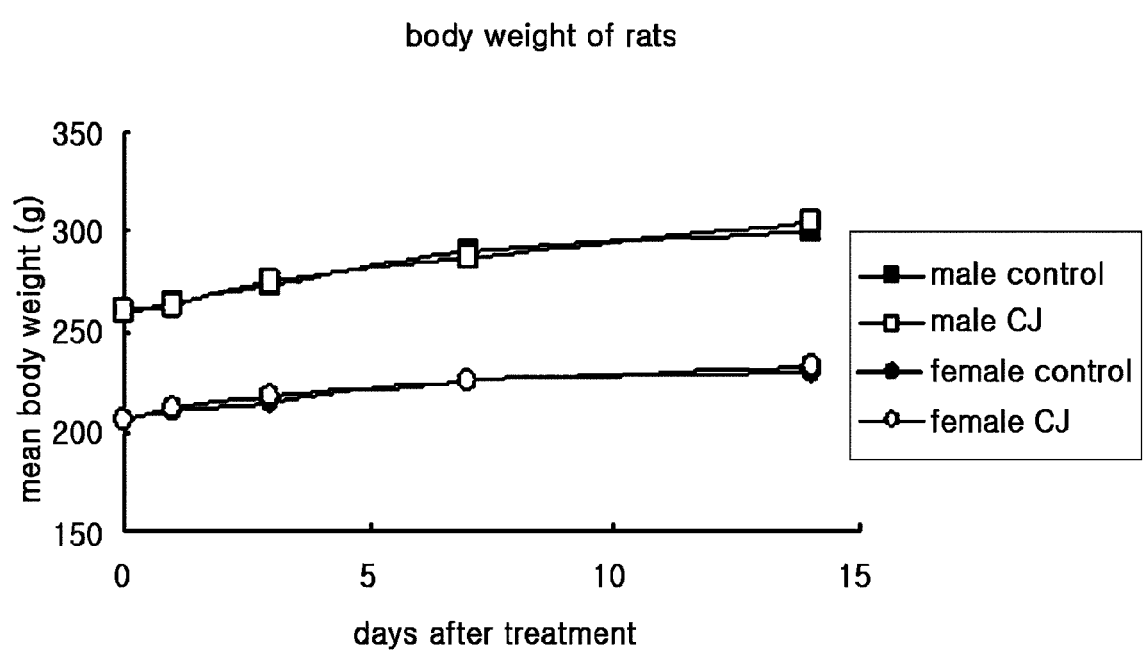
FIG. 9 is a graph in which body weights of rats are plotted against time 1, 3, 7, 10 and 14 days after administration and before the administration. with the bacteriophage ΦCJ7, showing that no significant changes in body weight were found in comparison with the control (■; male control, □; male test group administered with ΦCJ7, ●; female control, ○; female test group administered with ΦCJ7)

For safety use in the prevention of salmonellosis, *salmonella* food poisoning, fowl typhoid and pullorum, the bacteriophage was in vivo assayed for toxicity. Toxicity assay was performed with single oral dosages. In this assay, rats were orally administered with a single dosage of ΦCJ7 and monitored for acute toxicity to determine approximate lethal concentrations of ΦCJ7. To this end, first, specific-pathogen free (SPF) male and female rats (SD) 7 weeks old, each of 10, were starved for 24 hrs before administration with ΦCJ7. On the administration day, five males and five females were orally administered at a dose of 10 mL/kg with ΦCJ7 having a titer of $1 \times 10^{12}$ pfu/ml using an oral sonde while five controls were orally administered with a 20 mM Tris-HCl and 2 mM MgCl$_2$ mix. Four hrs after the oral administration, feeds were provided for rats. Monitoring was conducted every hour for 4 hours, starting from 30 min after the administration on the day of administration. Since then, they were monitored once a day for 14 days for general symptoms. None of them died. Neither toxic symptoms nor noticeable clinical symptoms were generated by ΦCJ7. The results are summarized in Tables 4 and 5, below. Body weights were recorded before and 1 3, 7, 10 and 14 days after administration. No significant changes were observed in body weight, indicating that ΦCJ7 does not cause a toxic reaction sufficient to reduce appetite or to change the body weight. These results are shown in FIG. 9. No noticeable abnormalities were found in any organ as examined by autopsy and with the naked eye. Therefore, the novel bacteriophage ΦCJ7 is non-toxic.

TABLE 4

Oral Toxicity Assay of ΦCJ7 in
Terms of Mortality and General Symptoms

| Sex | Done Pfu/kg | Final Mortality Male | Final Mortality Female | Clinical Signs Male | Clinical Signs Female |
|---|---|---|---|---|---|
| Male | Control | 0/5 | 0/5 | 0/5 | 0/5 |
|  | $10^{13}$ | 0/5 | 0/5 | 0/5 | 0/5 |
| Female | Control | 0/5 | 0/5 | 0/5 | 0/5 |
|  | $10^{13}$ | 0/5 | 0/5 | 0/5 | 0/5 |

TABLE 5

Oral Toxicity Assay of ΦCJ7 in Terms of Organ Abnormality

| Sex | Done (pfu/kg) | Gross finding | Frequency |
|---|---|---|---|
| Male | Control | N.A.D[a] | 5/5 |
|  | $10^{13}$ | N.A.D | 5/5 |
| Female | Control | N.A.D | 5/5 |
|  | $10^{13}$ | N.A.D | 5/5 |

[a] no abnormalities detected.

Example 13

Efficiency of Bacteriophage

In order to evaluate the efficacy of ΦCJ7 for use in the prevention and treatment of *Salmonella*-mediated diseases, the bacteriophage was assayed for ability to control *salmonella* in a chicken farm where 20,000 layers were bred under a strict condition against *salmonella* infection.

Drinking water containing ΦCJ7 at a concentration of $10^6$ pfu/L was provided for a total period of 25 days. First, it was supplied for 17 days. Then, ΦCJ7-free drinking water was provided for 10 days before re-starting to supply the ΦCJ7-containing drinking water for 8 days. Before and after the supply of ΦCJ7, *salmonella* monitoring was conducted for environments of straw bedding and dust and for development samples of chicks, feathers and egg shells. Before the supply of ΦCJ7, *salmonella* was detected at feathers of hatcheries and chicks, indicating that it is difficult to control *salmonella* in a large farm although *salmonella*-controlling facilities are operated therein. In contrast, after the supply of ΦCJ7, no *salmonella* bacteria were detected from the environments and the development samples. Therefore, the supply of ΦCJ7 in the form of drinking water was effective in the prevention of *salmonella* discharge and the control of *salmonella*. The results are summarized in Table 6, below.

TABLE 6

Disinfection Effect of ΦCJ7 on *Salmonella*

|  |  | Environment | | Development Sample | | |
|---|---|---|---|---|---|---|
|  | day | Straw bedding | Dust | Chick | Feather | Egg Shell |
| Before supply | −30 | − | − | − | + | − |
|  | −21 | + | + | − | + | − |
|  | −16 | − | − | + | − | − |
|  | −13 | − | − | − | + | − |
| Primary supply of ΦCJ7 | 0 | − | − | − | − | − |
|  | 2 | − | − | − | − | − |
|  | 4 | − | − | − | − | − |
|  | 6 | − | − | − | − | − |
|  | 8 | − | − | − | − | − |
|  | 10 | − | − | − | − | − |
|  | 12 | − | − | − | − | − |
|  | 14 | − | − | − | − | − |
|  | 16 | − | − | − | − | − |
| Supply Interruption | −10 | − | − | − | − | − |
|  | −7 | − | − | − | − | − |
|  | −4 | − | − | − | − | − |
|  | −1 | − | − | − | − | − |
| Secondray supply of ΦCJ7 | 0 | − | − | − | − | − |
|  | 2 | − | − | − | − | − |
|  | 4 | − | − | − | − | − |
|  | 6 | − | − | − | − | − |
|  | 8 | − | − | − | − | − |
|  | 9 | − | − | − | − | − |

Example 14

Efficiency of Bacteriophage as a Sanitizer

In order to evaluate the efficiency of the bacteriophage, as a cleaner against *salmonella*. For comparison, harasol (Yuhan Corporation, sodium hypochloride 4.6%, a sanitizer for poultry barns, banks and drinking water) was used as a control under the condition of light water, organic materials, and milk.

Figure 10:
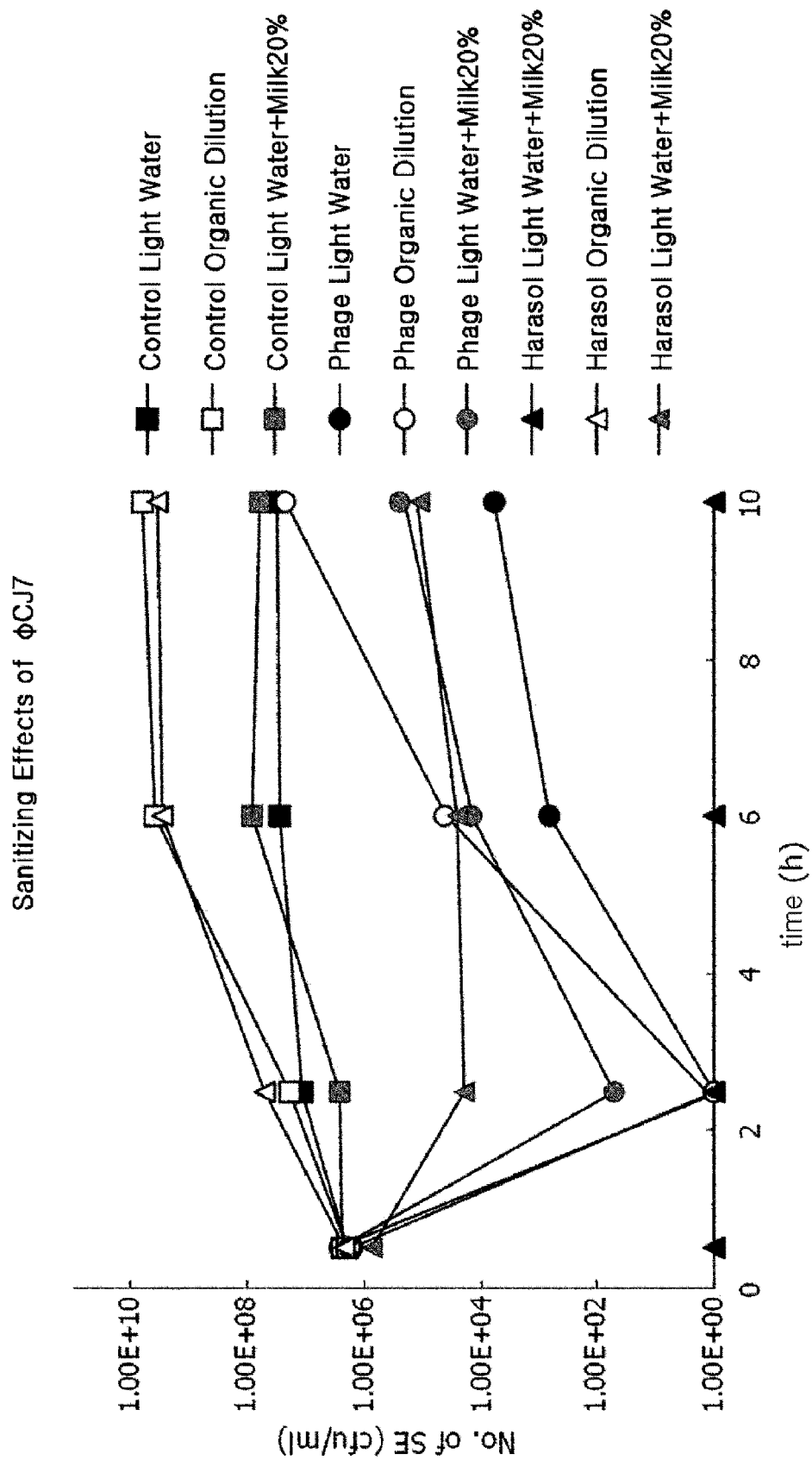
FIG. 10 is a graph showing the sanitizing effect of ΦCJ7. ΦCJ7 was observed to be effective in all conditions light water, organic dilution, and light water+20% milk. Particularly, the highest effect was obtained 2.5 hrs after treatment with ΦCJ7. The commercially available product Harasol (Yuhan Corporation, Korea), as a positive control, showed excellent effects in the condition of light water, but no effects on the organic dilution, and greatly reduced effect in the condition of light water+milk 20% (■; control light water, □; control organic dilution, control light water+milk 20%, ●; ΦCJ7 light water, ○; ΦCJ7 organic dilution, ΦCJ7 light water+milk 20%, ▲; Harasol light water, Δ; Harasol organic dilution, Harasol light water+milk 20%).

ΦCJ7 having a titer of $10^9$ pfu/ml, harasol (sodium hypochloride 4.6%), and SE strain were prepared. After being grown to O.D.=0.5, SE was 5-fold diluted in light water to give O.D.=0.1. Two 250 mL flasks, each containing 50 mL of light water, an organic material dilution, or a 20% milk dilution in light water, were prepared. The bacteriophage was added in an amount of $10^9$ pfu to one flask while a 1/240 dilution of the parasol was added to the other. To each flask was added 2 mL of the bacterial culture with O.D.=0.1, followed by incubation at 37° C. and 200 rpm with sampling at 0.5 h, 2.5 h, 6 h, and 10 h. The samples were serially diluted and spread over LB plates. After incubation at 37° C. for 18 hrs, the cells were counted to determine the bactericidal activity. When light water was used, the conventional sanitizer greatly fluctuated in antibacterial activity according to conditions. In contrast, the bacteriophage exerted uniform antibacterial activity even under various conditions. The results are shown in FIG. 10.

Example 15

Efficiency of Bacteriophage as a Cleaner

For use as a cleaner for meat product, the bacteriophage was assayed for ability to control *salmonella* bacteria in comparison with a conventional cleaner (4-6% Sodium hypochlorite). In this regard, 50 g of chicken breast cuts was purchased from a store. An SE shaking culture (O.D.=2) was adjusted to a concentration of $10^8$ cfu/ml and uniformly spread in an amount of 200 μL over the chicken breast cuts which were then dried at room temperature for 12 min. The bacteriophage ΦCJ7 loaded contained at a concentration of $10^9$ pfu/L, $10^{10}$ pfu/L, and $10^{11}$ pfu/L and 50 ppm in respective sprayers and the cleaner chlorine was contained at a concentration of 50 ppm in a sprayer. They were sprayed at a rate of one stroke/sec for 10 sec. The treated chicken breast cuts were placed in respective sanitary packs to which 30 mL of an SM buffer was then added. The packs were shaken in a semicircle pattern. The WCR (whole carcass rinse) thus obtained was serially diluted and the dilutions were spread over LB media, followed by incubation at 37° C. for 18 hrs to determine the number of SE. Immediately after treatment therewith, the cleaner was found to leave *salmonella* bacteria. However, the bacteriophage ΦCJ7 was identified as being very effective.

Further, with the lapse of time, the bacteriophage showed consistent cleaning activity, compared to the chemical. The results are summarized in Table 7, below.

TABLE 7

Comparison of Cleaning Efficiency between ΦCJ7 and Cleaner

| Time (min) | Substance | Reduction Rate of *Salmonella* (%) |
|---|---|---|
| 0 | SM buffer | |
| | PHI $10^9$ pfu/L | 3.70 |
| | PHI $10^{10}$ pfu/L | 1.27 |
| | PHI $10^{11}$ pfu/L | 48.09 |
| | Chlorine 50 ppm | (+14.50) |
| 30 | SM buffer | |
| | PHI $10^9$ pfu/L | 21.31 |
| | PHI $10^{10}$ pfu/L | 22.45 |
| | PHI $10^{11}$ pfu/L | 68.71 |
| | Chlorine 50 ppm | 9.52 |
| 200 | SM buffer | |
| | PHI $10^9$ pfu/L | 36.00 |
| | PHI $10^{10}$ pfu/L | 43.75 |
| | PHI $10^{11}$ pfu/L | 49.63 |
| | Chlorine 50 ppm | 12.59 |
| 1440 | SM buffer | |
| | PHI $10^9$ pfu/L | 24.39 |
| | PHI $10^{10}$ pfu/L | 60.58 |
| | PHI $10^{11}$ pfu/L | 73.33 |
| | Chlorine 50 ppm | 13.33 |

Having specific bactericidal activity against one or more *Salmonella* bacteria selected from the group consisting of *Salmonella* Enteritidis (SE), *Salmonella* Typhimurium (ST), *Salmonella* Gallinarum (SG), and *Salmonella* Pullorum (SP) without affecting beneficial bacteria, in addition to showing excellent tolerance to acid, heat and desiccation, as described hitherto, the novel bacteriophage of some embodiments of the present invention can be widely used as an active ingredient for therapeutic agents, animal feeds or drinking water, cleaners and sanitizers for preventing and treating the infectious diseases caused by *Salmonella* Enteritidis, *Salmonella* Typhimurium, *Salmonella* Gallinarum or *Salmonella* Pullorum including salmonellosis, *Salmonella* food poisoning, Fowl Typhoid, and Pullorum disease.

Although preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. An isolated bacteriophage having a specific bactericidal activity against one or more *Salmonella* bacteria selected from the group consisting of *Salmonella Enteritidis*, *Salmonella Typhimurium*, *Salmonella Gallinarum*, and *Salmonella Pullorum*, which is deposited under accession number KCCM11030P.

2. A composition for inhibition or treatment of infectious diseases caused by one or more *Salmonella* strains selected from the group consisting of *Salmonella Enteritidis*, *Salmonella Typhimurium*, *Salmonella Gallinarum*, and *Salmonella Pullorum*, comprising the bacteriophage of claim 1.

3. The composition according to claim 2, wherein the infectious diseases are salmonellosis and salmonella food poisoning when caused by *Salmonella enteritidis* or *Salmonella Typhimurium*, Fowl typhoid when caused by *Salmonella Gallinarum* and pullorum when caused by *Salmonella Pullorum*.

4. An antibiotic comprising the bacteriophage of claim 1.

5. An animal feed or drinking water, comprising the bacteriophage of claim 1.

6. A sanitizer and cleaner, comprising the bacteriophage of claim 1.

7. A method for inhibiting or treating infectious diseases caused by one or more *Salmonella* strains selected from the group consisting of *Salmonella Enteritidis*, *Salmonella Typhimurium*, *Salmonella Gallinarum*, and *Salmonella Pullorum*, comprising administering the bacteriophage of claim 1 to animals in need thereof.

8. A method for inhibiting or treating infectious diseases caused by one or more *Salmonella* strains selected from the group consisting of *Salmonella Enteritidis, Salmonella Typhimurium, Salmonella Gallinarum*, and *Salmonella* Pullorum, comprising administering the composition of claim 2 to animals in need thereof.

* * * * *

SEQUENCE LISTING

<160> NUMBER OF SEQ ID NOS: 16

<210> SEQ ID NO 1
<211> LENGTH: 1394
<212> TYPE: DNA
<213> ORGANISM: Bacteripharge KCCM11030P

```
<400> SEQUENCE: 1
cctatagtat cgaaaggcta ctcgatgacg cgaggtaaca acgtgtggcg agtagacctg      60
gccggtggcg gggttcgcca ggggcgtgat acatactttg atatgttccc gattaacgtt     120
accctggtcg tatcaccgtt ggggcggcaa gcattcctca gtttcatgga gaaggtagac     180 ggagggctt ccagtttctg gatgaaacac gacttgggtc agggtatcga ggattaccag      240
gttactctaa catctcgtg gaacgagtcc accgacgacg ggaagaactg ggtaataact      300
ttcacggcca cagccgagaa atcaccattc caggaagccg gcagcgcctg tcttaaccag     360
aatctgcccg acttatatgg atgctacggc gattgtcttg gtgaatttct aaaacttac      420 ggagtgtacc aaactacatt ccctcgaatc tgggacccaa tgcaatgagt caggaatcag     480
tagaagcggc ataccggcgt aagctggcgt ccaatcccga tggcgagatg gattttatta     540
ccctggagat atcccaccct cttctttcga agcgctggtt gcttgtgcgc ggggctaacg     600
acttgaccgc tactctagag acgggtgagg ttgttacatt cgagggtacg ccgatggagg     660
ccaagaacgc cgccaacaat aacgatatgg accagaccgc ctctttctct ttgccggatg     720
tgcttaatat actggacgag gaaatggacc gcatcccta tgataataag gaattgccca      780
aattcatctt ccggcgttac gtgagcacgg acctgtcata cccatgcgat gggccggtgg     840
tatatgaatt gcaaacactc acacaagaga aggagtgtt cacagcggaa acaggtacac      900
ccatgcttaa ccaacgagct accggaatcc tgatgacgcc ggaggagatt cctttacttc     960
gagggatact gacatcgtga atattaacga ttacactggc ctgccgtatg acttccgccg    1020
ccgtaattgt tggcaccacg tccgcaacgt ccgggctgac gcggggttat caactccaat    1080
gttcgatgta acaagcccaa cggcaataga tgcagctttc gatgacggcc attcagaccc    1140
taaaggtctt aggcgagtgc ttactccgca gaattttgac gccgttctac tcggtgtgaa    1200
acatcgaggg cggatagtgt ggcacgctgg ggtatattac gaagggatgg ttagccactg    1260
tgagctggcg tccagacagg ttagactgga tagtctggaa gaccttaaag atacttattc    1320
ggagattgaa ttttggcgct agtaattcac tacacacgaa acgaagacgg cacatttgac    1380
gttaaacgtt atcg                                                      1394

<210> SEQ ID NO 2
<211> LENGTH: 672
<212> TYPE: DNA
<213> ORGANISM: Bacteriopharge KCCM11030P

<400> SEQUENCE: 2
aaccgggagg tgtcgccgta ttatgcgtat aagttcgggg attgtatgat ttcagcacat      60
cacgggcatt gttctaactt tactaaagta gagcagtcta taataggtaa gtatcgggag     120
atgtacgggc agtgtaagtt cacatatgtc catacgggtc acctacacca ccgggcggtt     180
aaagagacta atcttctaat tgttgagcaa caccagacat tagcggctaa agatgagtat     240
tctagtaaag gcggttatta ttcaggtaga agcgcaaatg tgattacata ccataaacgt     300 tacgggagg tgtcccgcat aagtataccT gttgaaatgc tgcgagacat aaaccccaaa      360
tcaacatact aaaatgtagg tgaaaggatg gattggagtg aggtttttag ctacaaaaac     420
ggcgtcctat actggaaagt caaatcatgt cgccgtaacg atgtgaatgt agggggatgtg     480 gccgggagtt tgtgtaaaaa cggctattgg tatgtcatgt tcggtaaccg taagtttaaa    540
aggtctaggg tggtgtatga gatgttctca ggtaagattc caaaaggatt tgtcatagac    600
```

```
cacaccaacc atgatacctg tgacgacaga attgaaaacc tgtcatgcaa atccagaagg    660
gacaacatgg tt                                                       672
```

<210> SEQ ID NO 3
<211> LENGTH: 581
<212> TYPE: DNA
<213> ORGANISM: Bacteriopharge KCCM11030P

<400> SEQUENCE: 3

```
gacggatggc ttgctgcgtg atctggatgt gttctccacg tccggactgg ccttgccctg     60
gcgtaccgtc acgggatttc caacctcaag ctgaaacacg ccaaccacaa ataaaaatgc    120
catgccggat gcaacacatc cggcaacttc acacttactc gtccagcaga atcactttgc    180
cgatatacgg cagatgacgg taacgctgtg cgtaatcaat gccgtaaccc accacaaact    240
catccgggat cgagaaaccg ataaattcta ccgggacgtt cacttcacga cgggacggtt    300
tatccagcag cgtacaaatc gccagcgact tcggttcgcg caggcttaag atctcacgca    360
ctttcgacag tgtatccccg agtcgatgat atcttcaaca atcagcacgt ccttgccacg    420
gatatcttca tccagatctt tgaggatttt cacatcatgg gtggtggaca tgccgctacc    480
gtagctggag gcggtcataa agtcgacttc atgagatacc tgaacttcac ggcacaggtc    540
cgccataaac ataaatgagc cacgcagcaa ggcatcggtc a                        581
```

<210> SEQ ID NO 4
<211> LENGTH: 1008
<212> TYPE: DNA
<213> ORGANISM: Bacteriopharge KCCM11030P

<400> SEQUENCE: 4

```
acaggcaatt tagcatactc atggtcgcgt cgcaatcgcc gtgaggaacg cgctgacatt     60
aacgtttaca ccacgacctc cggcacctgg gatgagtttg ttgaacttat gcaaccgctt    120
aaacgttcgc gccggaaccc caagacagac cccggctaca ttaccgccgc ttgtaccgcc    180
acggtaagct ctaccggtaa agaagccgcc gaaggtatgt tctatcgctg caatgcgtct    240
gttacgtctt catccctggc ctatgccgac gtggacagcg cgacgccgga agagttcgca    300
accgactgtg agatggtgcg cgagtcacgt tacgcaatga tgctctacac cacggcatcc    360
cacaccgaag aagcgccgcg ctaccgcgtc gttatgcctg tacgcactcc ggtaaccggt    420
ggcgacatca tccgcatccg gtacggcctg ttggcacact tccttaaagg tcgtgacgtg    480
gatagcgccg ggttcaccct gtcgcagcct atgtaccgcc cgccggtagg aagccaggtc    540
atcgtgtctg aaagtagccg catgattacg gcgagcaagc ttatggagga agttcctgaa    600
attaacgtta ccggtgcttc tgattataaa gttccggagg gtgaacaatc cgaattaacc    660
gacctgtttg aagagttcgc ttttgaattc ggcggacgta tgaccgaccg cggcctgcaa    720
atgcccgcca cgccggagca cgccgcccaa tacactaccg gcgaacctaa gcaggacgac    780
ttcctgttct gttggccgcg cgacggcttc gagcgaccca cgttaccct gtaccacgat    840 accgacctgg tagctacggg cgggatgaag cctggcggac gggatatgtg ggcttacgct    900
tgtgcggcca ccggcttacc ttttgaccgt gtggagtgcc gcttgggtgg gcggagggg    960 tcacttgcga cgaagaagac ctggacgacg agaccaccag caccacaa               1008
```

<210> SEQ ID NO 5
<211> LENGTH: 18
<212> TYPE: DNA
<213> ORGANISM: Artificial Sequence

```
<220> FEATURE:
<223> OTHER INFORMATION: primer

<400> SEQUENCE: 5
cctatagtat cgaaaggc                                                    18

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6
cgataacgtt taacgtcaaa tg                                               22

<210> SEQ ID NO 7
<211> LENGTH: 18
<212> TYPE: DNA
<213> ORGANISM: Artificial Sequence
<220> FEATURE:
<223> OTHER INFORMATION: primer

<400> SEQUENCE: 7
aaccgggagg tgtcgccg                                                    18

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
aaccatgttg tcccttctgg                                                  20

<210> SEQ ID NO 9
<211> LENGTH: 18
<212> TYPE: DNA
<213> ORGANISM: Artificial Sequence
<220> FEATURE:
<223> OTHER INFORMATION: primer

<400> SEQUENCE: 9
gacggatggc ttgctgcg                                                    18

<210> SEQ ID NO 10
<211> LENGTH: 18
<212> TYPE: DNA
<213> ORGANISM: Artificial Sequence
<220> FEATURE:
<223> OTHER INFORMATION: primer

<400> SEQUENCE: 10
tgaccgatgc cttgctgc                                                    18

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
acaggcaatt tagcatactc                                                  20
```

```
<210> SEQ ID NO 12
<211> LENGTH: 22
<212> TYPE: DNA
<213> ORGANISM: Artificial Sequence
<220> FEATURE:
<223> OTHER INFORMATION: primer

<400> SEQUENCE: 12
ttgtggtgct ggtggttctt cg                                              22

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
cgggcctctt cgctattacg                                                 20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
aggcttaccc gtcttactgt                                                 20

<210> SEQ ID NO 15
<211> LENGTH: 17
<212> TYPE: DNA
<213> ORGANISM: Artificial Sequence
<220> FEATURE:
<223> OTHER INFORMATION: primer

<400> SEQUENCE: 15
gtaaaacgac ggccagt                                                    17

<210> SEQ ID NO 16
<211> LENGTH: 16
<212> TYPE: DNA
<213> ORGANISM: Artificial Sequence
<220> FEATURE:
<223> OTHER INFORMATION: primer

<400> SEQUENCE: 16
aacagctatg accatg                                                     16
```